US012753271B2

(12) United States Patent
Martinez et al.

(10) Patent No.: US 12,753,271 B2
(45) Date of Patent: Oct. 6, 2026

(54) BIO-FUNCTIONALIZATION OF WATER-SOLUBLE POLY(PHENYLENE EHTYLENE)S

(71) Applicant: Board of Regents, The University of Texas System, Austin, TX (US)

(72) Inventors: Daniel Martinez, San Antonio, TX (US); Han Sun, San Antonio, TX (US); Zhiliang Li, San Antonio, TX (US); Samantha Yee, San Antonio, TX (US); April Risinger, San Antonio, TX (US); Kirk Schanze, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 650 days.

(21) Appl. No.: 18/035,511

(22) PCT Filed: Nov. 9, 2021

(86) PCT No.: PCT/US2021/058666

§ 371 (c)(1),
(2) Date: May 4, 2023

(87) PCT Pub. No.: WO2022/099209

PCT Pub. Date: May 12, 2022

(65) Prior Publication Data

US 2023/0399455 A1 Dec. 14, 2023

Related U.S. Application Data

(60) Provisional application No. 63/198,740, filed on Nov. 9, 2020.

(51) Int. Cl.

*C08G 61/02* (2006.01)
*A61K 47/59* (2017.01)

(52) U.S. Cl.

CPC .............. *C08G 61/02* (2013.01); *A61K 47/59* (2017.08); *C08G 2261/124* (2013.01); *C08G 2261/1412* (2013.01); *C08G 2261/1426* (2013.01); *C08G 2261/1432* (2013.01); *C08G 2261/145* (2013.01); *C08G 2261/1522* (2013.01); *C08G 2261/18* (2013.01); *C08G 2261/312* (2013.01); *C08G 2261/94* (2013.01)

(58) Field of Classification Search

CPC .............. C08G 61/02; C08G 2261/124; C08G 2261/1412; C08G 2261/1426; C08G 2261/1432; C08G 2261/145; C08G 2261/1522; C08G 2261/18; C08G 2261/312; C08G 2261/94; A61K 47/59

USPC .......................................................... 528/205

See application file for complete search history.

(56) References Cited

U.S. PATENT DOCUMENTS

| | | | |
|---|---|---|---|
| 9,527,806 | B2 | 12/2016 | Whitten et al. |
| 2016/0206751 | A1 | 7/2016 | Moon et al. |

OTHER PUBLICATIONS

Kini et al., Adv. Mater. 2020, 32, 1906175.
Bronstein et al., Nat. Rev. Chem. 2020, 4, 66-77.
Kong et al., Polymers 2017, 9, 42.
(Continued)

*Primary Examiner* — David T Karst

(57) ABSTRACT

Certain embodiments are directed to the use of amide coupling chemistry to covalently link five different biofunctional groups onto an anionic water soluble poly(phenylene ethynylene) (PPE) polymer. Two of the biofunctionalized PPEs are used in prototype applications, including pH sensing and flow cytometry labeling.

12 Claims, 9 Drawing Sheets

(56) References Cited

OTHER PUBLICATIONS

Li et al., Acc. Chem. Res. 2016, 49, 78-85.
Fu et al., Angew. Chem., Int. Ed 2019, 58, 4442-4453.
Zhang et al., Chem. Soc. Rev. 2020, 49, 1331-1343.
Hwang et al., ACS Appl. Mater. Interfaces 2020, 12, 8485-8494.
Chen et al., Chem. Rev. 2020, 120, 2879-2949.
Chen et al., ACS Appl. Mater. Interfaces 2020, 12, 6144-6150.
Wang et al., Coard Chem. Rev. 2018, 354, 135-154.
Zhou et al., Acc. Chem. Res. 2019, 52, 3211-3222.
Anantha-Iyengar et al., Frog. Polym. Sci. 2019, 88, 1-129.
Zhang et al., Macromolecules 2006, 39, 7839-7843.
Jagadesan and Schanze, Macromolecules 2019, 52, 3845-3851.
Stratton et al., Chem.-Eur.J 2017, 23, 14064-14072.
Chen et al., Chem. Rev. 2012, 112, 1910-1956.
Xia et al., Anal. Chem. 2017, 89, 1238-1243.
Lee et al., Macromolecules 2011, 44, 4742-4751.
Jiang et al., Langmuir 2006, 22, 5541-5543.
Feng et al., Adv. Funct. Mater., 2016, 26, 7431-7442.
Banfić et al., Eur. J. Inorg. Chem., 2014, 2014, 484-492.
Jagadesan et al., Mater. Chem. Front., 2020, 4, 3649-3659.
Damavandi et al., European Polymer Journal 98, 2018, 368-374.
Philips et al., J.AM. Chem. Soc., 2008, 130, 6952-6954.
Ogoshi et al., Chem. Commun., 2006, 3702-3704.
Bunz, Macromal. Rapid Commun., 2009, 30, 772-805.
Atkins et al., Can. J. Chem. 89, 47-56, 2011.
Sun et al., ACS Appl. Mater. Interfaces 2020, 12, 53310-53317.

BIO-FUNCTIONALIZATION OF WATER-SOLUBLE POLY(PHENYLENE EHTYLENE)S

PRIORITY PARAGRAPH

This application claims priority to International Application PCT/US2021/058666 filed Nov. 9, 2021 which claims priority to U.S. Provisional Application Ser. No. 63/198,740 filed Nov. 9, 2020, each of which is incorporated herein by reference in its entirety.

STATEMENT REGARDING FEDERALLY FUNDED RESEARCH

None.

BACKGROUND

Conjugated polymers are comprised of delocalized π-conjugated backbones and modifiable side-chains. Through rational design of the backbone and side-chain structures, the physical and material properties of conjugated polymers can be tuned on demand, enabling them to be widely used as active components of optoelectronic devices,[1,2] including organic solar cells,[3-5] organic light emitting diodes,[6,7] and organic field effect transistors.[8,9] The introduction of water-solubilizing groups (such as amino groups, quaternary ammonium groups, imidazolium groups, carboxylic groups, sulfonic groups, and phosphate groups) to the side-chains enables application of conjugated polymers to problems in the biomedical area.[10] The ionic side-chains not only allow the polymers to disperse well in aqueous solution under physiological conditions, but they also provide electrostatic binding sites for a wide variety of biomolecules, including proteins and nucleic acids. Furthermore, introduction of functional groups into conjugated polymers can lead to materials that are perfectly designed for specialty applications. From small functional molecules, such as biotin,[11,12] rhodamine,[13,14] folic acid[15,16] to biomacromolecules including DNA,[17] antibodies,[18] and lipids,[19] various molecules have been linked to or otherwise incorporated within conjugated polymer structures, for applications such as biosensing, imaging and therapy.[20,21] Although many achievements have been made, the linking or attachment of bio-functional units onto conjugated polymers in a facile, controlled, and mild manner remains a challenge. In addition, a general approach to introducing a variety of functionalities onto water-soluble conjugated polymer platforms has not been previously reported.

There are two methods to prepare functionalized conjugated polymers, monomer functionalization prior to polymerization, and post-polymerization functionalization of the polymer. Post-polymerization functionalization is generally advantageous because it enables the synthesis of polymer libraries with consistent molecular weight and polydispersity, and it also avoids the possible negative influence of reactive functional groups on the polymerization reactions.

There remains a need for additional methods for coupling ligands to conjugated polymers.

SUMMARY

Embodiments described herein provide a solution for linking or attachment of bio-functional units onto conjugated polymers in a facile, controlled, and mild process.

Certain embodiments are directed to the use of amide coupling chemistry to covalently link five different biofunctional groups onto an anionic water soluble poly(phenylene ethynylene) (PPE) polymer. Two of the biofunctionalized PPEs are used in prototype applications, including pH sensing and flow cytometry labeling. The PPE is functionalized with carboxylate ($R—CO_2^-$) and sulfonate ($R—SO_3^-$) ionic groups. By using an activated ester, the amine functionalized groups are covalently linked to the PPE polymer via amide linkages. The reaction chemistry is optimized using biotin-ethylene diamine, making it possible to control the loading of the biotin functionality on the PPE chains. Using the optimized approach, an example of a family of five PPEs were prepared that contain biotin, rhodamine, cholesterol, mannose, or folic acid moieties appended to the polymer backbones. The rhodamine and biotin modified PPEs were further applied for pH response and flow cytometry applications. The approach can be utilized for other classes of water-soluble conjugated polymers, allowing facile development of a variety of new functionalized water-soluble conjugated polymers for a range of applications including sensing, bioimaging, and flow cytometry analysis.

Certain embodiments are directed to a water-soluble polymer conjugate comprising a base polymer coupled to one more ligands having a structure of Formula III Formula III

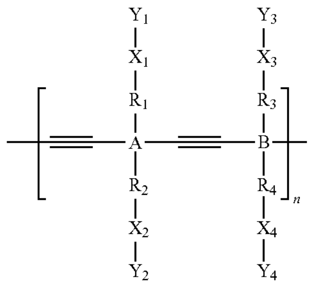

wherein n can be any whole number between 2 and 500; A and B are aryl or heteroaryl; R1, R2, R3, and R4 are independently selected from a C1 to C12 alkoxy, C1 to C12 alkyl, and (CH2CH2O)m, where m is 2, 3, 4, 5, 6, 7, 8, 9, 10; X1, X2, X3, and X4 are independently selected from amino, quaternary ammonium, imidazolium, carboxylic, sulfonic, phosphate, and phosphonium; and Y1, Y2, Y3, and Y4 can be H or a ligand. In certain aspects A and B are phenyl. In other aspects R1 and R2 are C1 alkoxy and R3 and R4 are C3 alkoxy. In certain aspects X1 and X2 are carboxyl groups and X3 and X4 are sulfonic groups. In other aspects Y1, Y2, Y3, and Y4 are independently selected from a H, a detectable ligand, therapeutic ligand, or a diagnostic ligand. The polymer conjugate can have 1, 2, 3, 4, 5, or more different ligands conjugated to the polymer. In certain aspects 1 up to 2000 ligands in total can be conjugated to a polymer. In certain aspects 1, 2, 3, 4, 5, 6, 7, 8, 9, 10, or more different ligands are conjugated to the polymer. The ligand can be coupled to the polymer by a linker. The linker can be a non-labile or labile linker. In certain aspects the labile linker is a photo-labile linker. The polymer conjugate can be a prodrug.

Certain embodiments are directed to therapeutic methods comprising administering a therapeutic conjugate to a subject in need thereof.

Other embodiments are directed to analytical methods comprising contacting a sample with a detectable conjugate and detecting a signal derived from the polymer conjugate.

Certain embodiments are directed to diagnostic methods comprising administering a diagnostic conjugate to a subject or sample and detecting a signal derived from the conjugate to evaluate a subject, environment, or condition.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

Figures 8A, 8B:
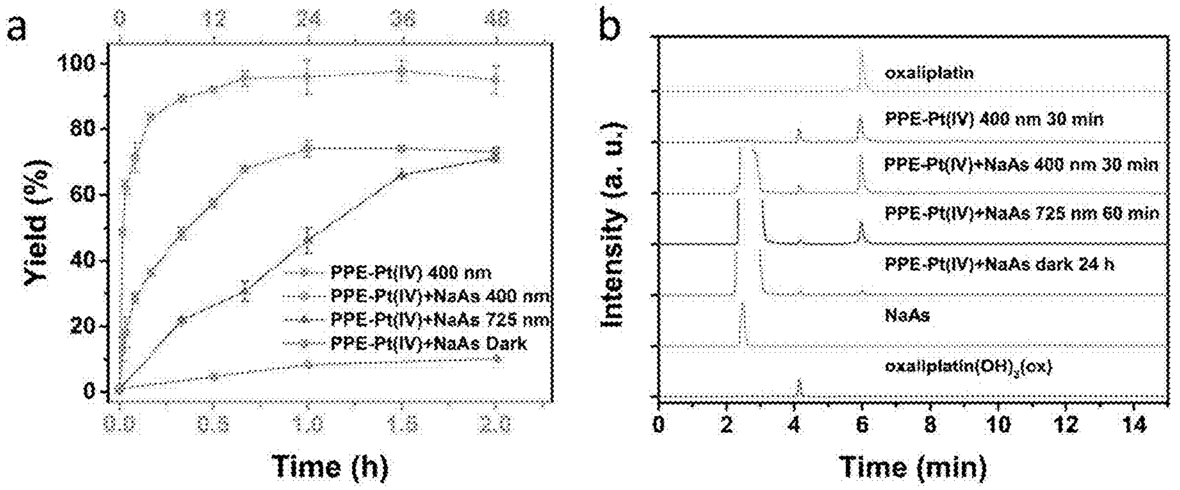

FIG. 8*a*-8*b*. (a) The chemical yield of oxaliplatin upon photolysis of PPE-Pt(IV) (50 μM) or dark treatment of PPE-Pt(IV) (50 μM) with NaAs (1 mM). The power density of 400 nm LED is 5 mW/$cm^2$. (b) HPLC (270 nm) chromatograms of oxaliplatin (25 μM); PPE-Pt(IV) (50 μM) irradiated with a 400 nm LED light for 30 min); PPE-Pt(IV) (50 μM) irradiated with a 725 nm laser for 60 min; PPE-Pt (IV) (50 μM) with NaAs (1 mM) in the dark for 24 h; NaAs (20 μM), and oxaliplatin(OH) 2 (ox)(15 μM).

Figures 9A, 9B, 9C:
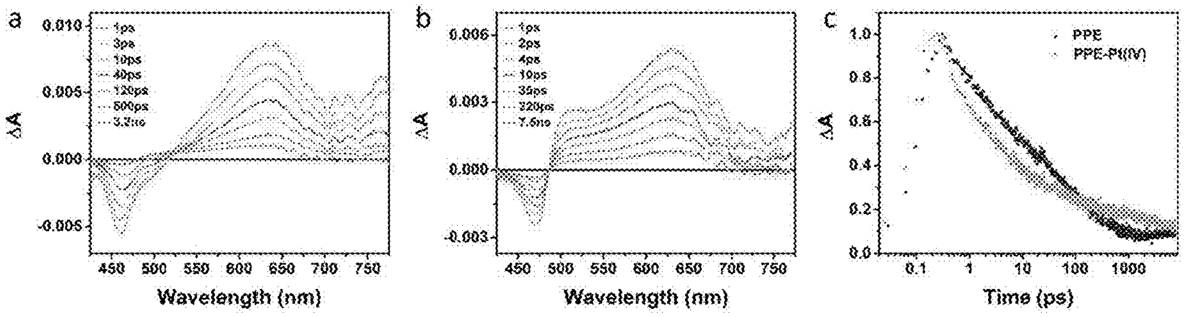

FIG. 9*a*-9*c*. Picosecond transient absorption (psTA) spectra of (a) PPE and (b) PPE-Pt(IV) in water at the indicated delay times following a 405 nm laser excitation pulse (100 fs pulse width, 100 n7/pulse). (c) Kinetic decay traces of PPE and PPE-Pt(IV) detected at 661 nm.

FIG. 10*a*-10*d*. Light-dependent effects of PPE-Pt(IV) on viability and DNA damage in SK-OV-3 human ovarian cancer cells. (a, b) Percent viability of SK-OV-3 cells after incubation with PPE-Pt(IV), PPE, or oxaliplatin at indicated concentrations (repeat unit) for 24 h prior to 20 min light activation at 460 nm with a power density of 7.0 mW/$cm^2$. Cell viability as compared to vehicle treated controls was measured by the sulforhodamine B(SRB) assay after cells were incubated for an additional 48 h after light activation either without (a) or with (b) removal of residual compound in the media (n=2-5 independent experiments). (c) Percent viability of SK-OV-3 cells after incubation with PPE-Pt(IV), PPE, or oxaliplatin at indicated concentrations for 1 h prior to 20 min light activation at 460 nm with a power density of 7.0 mW/$cm^2$. Cell viability as compared to vehicle treated controls was measured by the SRB assay after cells were incubated for an additional 48 h after light activation without removal of residual compound in the media (n=3 independent experiments). Statistical significance in a-c determined by two-way ANOVA with Dunnett's post hoc test for multiple comparisons with significance compared to PPE-Pt(IV) light at each concentration indicated (d) Nuclear intensity of γH2A.X (P-Ser139) per cell was measured by immunofluorescence after incubation with vehicle, PPE-Pt (IV), or oxaliplatin at the indicated concentration for 1 h prior to light activation and incubation for an additional 18 h post-activation. Statistical significance determined by one-way ANOVA with Tukey's post hoc test for multiple comparisons (n=3 wells per condition with closed circles representing individual wells). ** $p<0.0001$, * $p=0.0003$, ** $p<0.01$, and * $p<0.05$.

DESCRIPTION

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be an example of that embodiment, and not intended to imply that the scope of the disclosure, including the claims, is limited to that embodiment.

As proof of principle the inventors have designed and synthesized a novel water-soluble PPE-based conjugated polymer with carboxylate group and sulfonate group side-chains. The polymer was used as a platform for post-polymerization functionalization through the amidation of carboxylate group with amine bearing functional molecules via an optimized procedure. Biotin, rhodamine, folic acid, mannose, and cholesterol were incorporated into PPE side-chains to demonstrate the versatility of the developed functionalization method. PPE-biotin and PPE-rhodamine were further employed to study their applications in pH sensing and flow cytometry. This work provides various examples of methods for post-polymerization functionalization of PPE derivatives with desired functional groups in a simple, general and controlled manner. This approach can also be potentially utilized for other types of water-soluble conjugated polymers, which allows for the facile development of many new functionalized water-soluble CPEs and exploring new applications.

I. POLY ETHYNYLENE (PE), POLY(ARLYLENE ETHYNYLENE)(PAE), POLY(PHENYLENE ETHYNYLENE)(PPE) AND CONJUGATES THEREOF

Poly(phenylene ethynylenes) (PPEs) are polymers that have a wide range of applications in electrically conducting materials, bio-chemical sensors, and supramolecular assemblies. The present disclosure provides a plurality of compounds generally referred to herein as poly (phenylene ethynylene) conjugates (PPE-conjugates, i.e., conjugated polymers with an attached or conjugated ligand), methods of synthesizing PPE conjugates and various uses for the PPE conjugates. The term conjugated polymer refers to the base polymer while the term polymer conjugate refers to the base polymer with an attached ligand. A generic structure for the polymer poly ethynylene is provided in Formula I Formula I

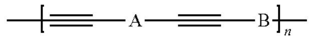

wherein A and B can be independently selected from substituted, saturated or unsaturated C3 to C6 cycloalkyl (including aromatics) or substituted, saturated or unsaturated C3 to C6 heterocyclyl, or polycyclic moiety including heteropolycycles. In certain aspects A, B, or A and B are a substituted aryl or substituted heteroaryl. In certain aspects the cycloalkyl is a substituted phenyl or substituted cyclohexane. In other aspects the heterocyclyl is a substituted saturated or unsaturated C6 heterocyclyl. In certain aspects A and B are the same; and n can be any whole number between 2 and 500.

In certain aspects a poly(phenylene ethynylene) as described herein can have a general structure of Formula Ia with n being between 2 to 500. In certain aspects the phenyl group can be substituted phenyl groups.

Formula Ia

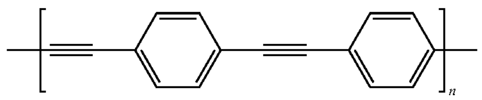

In certain embodiments water-solubilizing groups (such as an amino group (—$NH_2$), a quaternary ammonium group (—NR'R"R'"), an imidazolium group ($C_3H_5N_2$), a carboxylic group (COOH), a sulfonic group (—SOOH), a phosphate group (—$PO_3$), phosphonium (—$PH_3^+$), or similar functionalities) are introduced into the side-chains of a substituted aryl group (e.g., substituted phenyl) enabling the polymers to form a functionalized PE or PPE. The functionalized PE or PPE can be further attached or coupled to various ligands. Accordingly, an embodiment, the present disclosure provides functionalized polymers having a general structure of Formula II Formula II

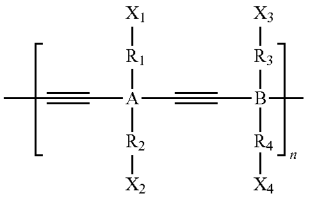

wherein n can be any whole number between 2 and 500. A and B can be independently selected from substituted, saturated or unsaturated C3 to C6 cycloalkyl (including aromatics) or C3 to C6 heterocyclyl, or polycyclic moiety including heteropolycycles. In certain aspects the cycloalkyl is a substituted phenyl or substituted cyclohexane. In other aspects the heterocyclyl is a substituted saturated or unsaturated C6 heterocyclyl. In certain aspects A, B, or A and B are aryl or heteroaryl. In certain aspects A and B are the same. In particular aspects, A and B are phenyls. R1, R2, R3, and R4 are independently selected from a C1 to C12 alkoxy, C1 to C12 alkyl, and $(CH_2CH_2O)m$, where m is 2, 3, 4, 5, 6, 7, 8, 9, 10; and X1, X2, X3, and X4 are independently selected from amino, quaternary ammonium, imidazolium, carboxylic, sulfonic, phosphate, and phosphonium. In certain aspects at least one of X1, X2, X3, and X4 is COOH. In certain aspects X1, X2, X3, and X4 are independently COOH or $SO_3$. In particular aspects the COOH is functionalized further by N or S (CONN or COSH).

In certain aspects a functionalized polymers can have the structure of Formula Ha wherein n is 2 to 500; and Z is N, O, or S. In particular aspects Z is N. In other aspects Z is 0.

Formula IIa

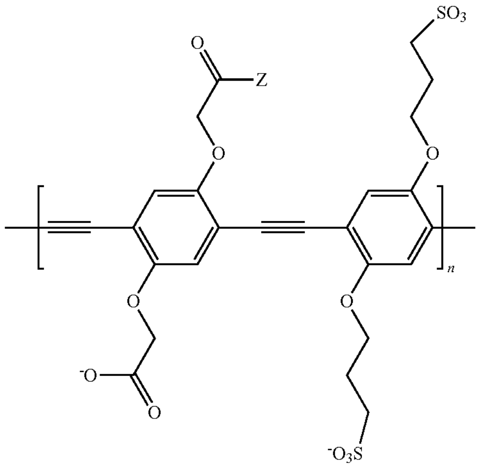

The functionalized polymers can be further attached or coupled (i.e., conjugated) to various ligands. In other embodiments a polymer conjugate can have a general structure of Formula III Formula III

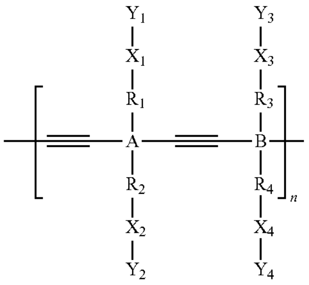

wherein n can be any whole number between 2 and 500; and A and B can be independently selected from substituted C3 to C6 cycloalkyl or C3 to C6 heterocyclyl, or polycyclic moiety including heteropolycycles. In certain aspects the cycloalkyl is a substituted phenyl or substituted cyclohexane. In other aspects the heterocyclyl is a substituted saturated or unsaturated C6 heterocyclyl. In certain aspects A, B, or A and B are aryl or heteroaryl. In certain aspects A and B are the same In particular aspects A and B are phenyl. R1, R2, R3, and R4 are independently selected from a C1 to C12 alkoxy, C1 to C12 alkyl, and $(CH_2CH_2O)m$, where m is 2, 3, 4, 5, 6, 7, 8, 9, 10; and X1, X2, X3, and X4 are independently selected from amino, quaternary ammonium, imidazolium, carboxylic, sulfonic, phosphate, and phosphonium. In certain aspects at least one of X1, X2, X3, and X4 is COOH. In certain aspects Y1, Y2, Y3, and Y4 can be H or a ligand. In certain aspects the ligand can be a detectable moiety, a diagnostic moiety, or a therapeutic moiety. In certain aspects 1, 2, 3, 4, 5, or more different ligands can be coupled to a polymer. The ligand can be but does not need be coupled by a linker. In certain aspects the attachment can be reversible forming a labile conjugate. Such labile conjugates can be used as a prodrug to deliver inactive or attenuated ligands to a location where the ligand is uncoupled an activated. For example, the ligand can be coupled to the polymer by a photolabile linker that can be irradiated dissociating the ligand from the polymer.

One example of a conjugate described here can have a structure of Formula Ma or IIIb.

Formula IIIa

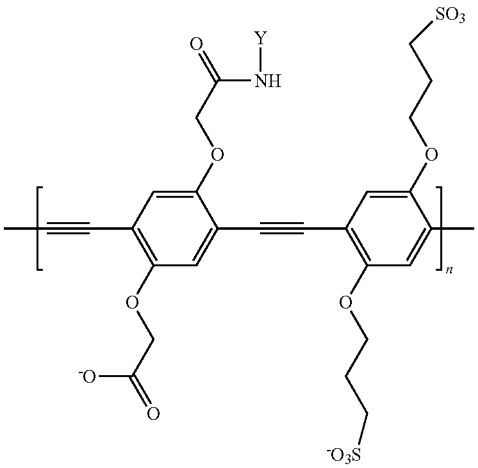

-continued

Formula IIIb

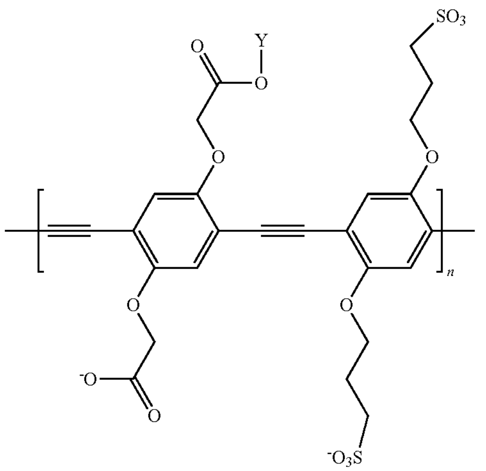

wherein n is any whole number between 2 and 200 and Y is a ligand.

Various chemical definitions related to such compounds are provided as follows.

As used herein, the term "water soluble" means that the compound dissolves in water at least to the extent of 0.010 mole/liter or is classified as soluble according to literature precedence.

As used herein, the term "nitro" means —NO 2; the term "halo" designates —F, —Cl, —Br or —I; the term "mercapto" means —SH; the term "cyano" means —CN; the term "azido" means —$N_3$; the term "silyl" means —$SiH_3$, and the term "hydroxy" means —OH.

The term "alkyl," by itself or as part of another substituent, means, unless otherwise stated, a linear or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, —$CH_3$ (Me), —$CH_2CH_3$(Et), —$CH_2CH_2CH_3$ (n-Pr), —$CH(CH_3)_2$ (iso-Pr), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, $CH_2CH_2OC(O)CH_3$, —$CH_2CH_2NHCO_2C(CH_3)_3$, and —$CH_2Si(CH_3)_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups can be described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl) 2 amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl.

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "alkylsulfonyl" as used herein means a moiety having the formula —$S(O_2)$—R', where R' is an alkyl group. R' may have a specified number of carbons (e.g., "$C_{1-4}$ alkylsulfonyl")

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare salts or pharmaceutically acceptable salts include: hydrochloric acid, phosphoric acid, sulfuric acid, hydrobromic acid, hydroiodic acid, phosphorous acid and the like. Examples of organic acids which may be used to prepare salts or pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like.

Suitable salts or pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

In certain aspects, salts having a positively charged counterion can include any suitable positively charged counterion. For example, the counterion can be ammonium ($NH_4^+$), H or an alkali metal such as sodium ($Na^+$), potassium ($K^+$), or lithium ($Li^+$). In some embodiments, the counterion can have a positive charge greater than +1, which can in some embodiments complex to multiple ionized groups, such as $Zn^{2+}$, $Al^{3+}$, or alkaline earth metals such as $Ca^{2+}$, or $Mg^{2+}$. Salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than ~1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

II. POLYMER CONJUGATES

The polymers described herein can be used to form functionalized water-soluble conjugated polymers. Moieties conjugated to the polymers described herein include, but are not limited to, therapeutic or diagnostic moieties or ligands. The conjugated moieties are referred to as ligands generally. A "ligand" is defined herein to be a molecule or part of a molecule that binds with specificity to another molecule. One of ordinary skill in the art would be familiar with the numerous agents that can be employed as targeting ligands in the context of the present invention. The targeting ligand can be any such molecule known to those of ordinary skill in the art. In certain aspects the ligand can be a drug or a targeting ligand/drug. Non-limiting examples of ligands are described herein. There may be overlap among ligand groups: for example, a particular compound may be both an agent that mimics glucose and a receptor marker. In certain aspects the ligand can be reversibly coupled to the PPE, that is the ligand can be a labile conjugate. In other aspects the ligand remains coupled to PPE under particular conditions of use (non-labile conjugate).

A. Ligands

Ligands can be broadly selected. In some embodiments the ligand can be selected from one or more drugs, vaccines, aptamers, avimer scaffolds based on human A domain scaffolds, diabodies, camelids, shark IgNAR antibodies, fibronectin type III scaffolds with modified specificities, antibodies, antibody fragments, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, microRNA, DNA, cDNA, antisense constructs, ribozymes, etc., and combinations thereof). In one embodiment, the ligand can be selected from proteins, peptides, polypeptides, soluble or cell-bound, extracellular or intracellular, kinesins, molecular motors, enzymes, extracellular matrix materials and combinations thereof. In another embodiment, bioactive agents can be selected from nucleotides, oligonucleotides, polynucleotides, and nucleic acids (e.g., mRNA, tRNA, snRNA, RNAi, DNA, cDNA, antisense constructs, ribozymes etc. and combinations thereof). In another embodiment, ligands can be selected from steroids, lipids, fats and combinations thereof. For example, the ligand can bind to the extracellular matrix, such as when the extracellular matrix is hyaluronic acid or heparin sulfate proteoglycan and the ligand is a positively charged moiety such as choline for non-specific, electrostatic, Velcro type binding interactions. In another embodiment, the ligand can be a peptide sequence that binds non-specifically or specifically.

Ligands can be but are not limited to peptides, proteins (e.g., antibodies or monoclonal antibodies), nucleic acids (e.g., antisense, siRNA, mRNA, microRNA, DNA, expression cassettes), small molecules (e.g., drugs), carbohydrates, lipids, and combinations thereof.

In some embodiments of the compositions of the present invention, a ligand is a therapeutic ligand or drug. A "therapeutic ligand" is defined herein to refer to any therapeutic agent or drug. A "therapeutic agent" or "drug" is defined herein to include any molecule or substance that can be administered to a subject, or contacted with a cell or tissue, for the purpose of treating a disease or disorder, or preventing a disease or disorder, or treating or preventing an alteration or disruption of a normal physiologic process. For example, a therapeutic ligand may be an anti-cancer moiety, such as a chemotherapeutic agent.

Examples of such moieties include, but are not limited to, a polypeptide, a nucleic acid molecule, a small molecule, a fluorophore, fluorescein, rhodamine, a radionuclide, indium-111, technetium-99, carbon-11, carbon-13, or a combination thereof. A therapeutic moiety can confer a therapeutic activity which include agents that are detrimental to a cell or agents that alter the activity of a cell. The therapeutic moiety can be selected from the group consisting of an alkylating agent or an anti-tumor antibiotic. Other examples of therapeutic moieties include cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286. In certain aspects the moiety can be a biotin, rhodamine, cholesterol, mannose, or folic acid moiety.

In certain aspects the moiety can be a detectable moiety. Examples of such moieties include, but are not limited to, a polypeptide, a nucleic acid molecule, a small molecule, a fluorophore, fluorescein, rhodamine, a radionuclide, indium-111, technetium-99, carbon-11, carbon-13, or a combination thereof.

Drugs. In another embodiment, the ligand can also be selected from specifically identified drug or therapeutic agents, including but not limited to: tacrine, memantine, rivastigmine, galantamine, donepezil, levetiracetam, repaglinide, atorvastatin, alefacept, tadalafil, vardenafil, sildenafil, fosamprenavir, oseltamivir, valacyclovir and valganciclovir, abarelix, adefovir, alfuzosin, alosetron, amifostine, amiodarone, aminocaproic acid, aminohippurate sodium, aminoglutethimide, aminolevulinic acid, aminosalicylic acid, amlodipine, amsacrine, anagrelide, anastrozole, aprepitant, aripiprazole, asparaginase, atazanavir, atomoxetine, anthracyclines, bexarotene, bicalutamide, bleomycin, bortezomib, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daptomycin, daunorubicin, deferoxamine, dexamethasone, diclofenac, diethylstilbestrol, docetaxel, doxorubicin, dutasteride, eletriptan, emtricitabine, enfuvirtide, eplerenone, epirubicin, estramustine, ethinyl estradiol, etoposide, exemestane, ezetimibe, fentanyl, fexofenadine, fludarabine, fludrocortisone, fluorouracil, fluoxymesterone, flutamide, fluticazone, fondaparinux, fulvestrant, gamma-hydroxybutyrate, gefitinib, gemcitabine, epinephrine, L-Dopa, hydroxyurea, icodextrin, idarubicin, ifosfamide, imatinib, irinotecan, itraconazole, goserelin, laronidase, lansoprazole, letrozole, leucovorin, levamisole, lisinopril, lovothyroxine sodium, lomustine, mechlorethamine, medroxyprogesterone, megestrol, melphalan, memantine, mercaptopurine, mequinol, metaraminol bitartrate, methotrexate, metoclopramide, mexiletine, miglustat, mitomycin, mitotane, mitoxantrone, modafinil, naloxone, naproxen, nevirapine, nicotine, nilutamide, nitazoxanide, nitisinone, norethindrone, octreotide, oxaliplatin, palonosetron, pamidronate, pemetrexed, pergolide, pentostatin, pilcamycin, porfimer, prednisone, procarbazine, prochlorperazine, ondansetron, palonosetron, oxaliplatin, raltitrexed, rosuvastatin, sirolimus, streptozocin, pimecrolimus, sertaconazole, tacrolimus, tamoxifen, tegaserod, temozolomide, teniposide, testosterone, tetrahydrocannabinol, thalidomide, thioguanine, thiotepa, tiotropium, topiramate, topotecan, treprostinil, tretinoin, valdecoxib, celecoxib, rofecoxib, valrubicin, vinblastine, vincristine, vindesine, vinorelbine, voriconazole, dolasetron, granisetron, formoterol, fluticazone, leuprolide, midazolam, alprazolam, amphotericin B, podophylotoxins, nucleoside antivirals, aroyl hydrazones, sumatriptan, eletriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, gatifloxacin, gemifloxacin, grepafloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecia, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, salmeterol, ipratropium bromide, flunisolide, cromolyn sodium, and ergotamine tartrate; taxanes such as paclitaxel; SN-38, and tyrphostines. Bioactive agents may also be selected from the group consisting of aminohippurate sodium, amphotericin B, doxorubicin, aminocaproic acid, aminolevulinic acid, arninosalicylic acid, metaraminol bitartrate, pamidronate disodium, daunorubicin, levothyroxine sodium, lisinopril, cilastatin sodium, mexiletine, cephalexin, deferoxamine, and amifostine in another embodiment.

Diagnostic Agents. Diagnostic agents useful in the polymer conjugates of the present invention include imaging agents and detection agents such as radiolabels, fluorophores, dyes and contrast agents. Imaging agent refers to a label that is attached to the random copolymer of the present invention for imaging a tumor, organ, or tissue in a subject. The imaging moiety can be covalently or non-covalently attached to the random copolymer. Examples of imaging moieties suitable for use in the present invention include, without limitation, radionuclides, fluorophores such as fluorescein, rhodamine, Texas Red, Cy2, Cy3, Cy5, and the AlexaFluor (Invitrogen, Carlsbad, Calif.) range of fluorophores, antibodies, gadolinium, gold, nanomaterials, horseradish peroxidase, alkaline phosphatase, derivatives thereof, and mixtures thereof.

Radiolabel refers to a nuclide that exhibits radioactivity. A "nuclide" refers to a type of atom specified by its atomic number, atomic mass, and energy state, such as carbon 14 (14C). "Radioactivity" refers to the radiation, including alpha particles, beta particles, nucleons, electrons, positrons, neutrinos, and gamma rays, emitted by a radioactive substance. Radionuclides suitable for use in the present invention include, but are not limited to, fluorine 18 (18F), phosphorus 32 (32P), scandium 47 (47Sc), cobalt 55 (55Co), copper 60 (60Cu), copper 61 (61Cu), copper 62 (62Cu), copper 64 (64Cu), gallium 66 (66Ga), copper 67 (67Cu), gallium 67 (67Ga), gallium 68 (68Ga), rubidium 82 (82Rb), yttrium 86 (86Y), yttrium 87 (87Y), strontium 89 (89Sr), yttrium 90 (90Y), rhodium 105 (105Rh), silver 111 (111Ag), indium 111 (111In), iodine 124 (1241), iodine 125 (1251), iodine 131 (1314 tin 117m (117mSn), technetium 99m (99mTc), promethium 149 (149Pm), samarium 153 (153Sm), holmium 166 (166Ho), lutetium 177 (177Lu), rhenium 186 (186Re), rhenium 188 (188Re), thallium 201 (201Tl) astatine 211 (211At), and bismuth 212 (212Bi). As used herein, the "m" in 117mSn and 99mTc stands for meta state. Additionally, naturally occurring radioactive elements such as uranium, radium, and thorium, which typically represent mixtures of radioisotopes, are suitable examples of radionuclides. 67Cu, 1311, 177Lu, and 186Re are beta- and gamma-emitting radionuclides. 212Bi is an alpha- and beta-emitting radionuclide. 211At is an alpha-emitting radionuclide. 32P, 47Sc, 89Sr, 90Y, 105Rh, 111Ag, 117mSn, 149Pm, 153Sm, 166Ho, and 188Re are examples of beta-emitting radionuclides. 67Ga, 111In, 99mTc, and 201T1 are examples of gamma-emitting radionuclides. 55Co, 60Cu, 61Cu, 66Ga, 68Ga, 82Rb, and 86Y are examples of positron-emitting radionuclides. 64Cu is a beta- and positron-emitting radionuclide.

Chemotherapeutic Agents as Ligands. A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of anti-cancer ligands include any chemotherapeutic agent known to those of ordinary skill in the art. Examples of such chemotherapeutic agents include, but are not limited to, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing. In certain particular embodiments, the anti-cancer ligand is methotrexate.

Other examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, canninomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMF0); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

Angiogenesis Targeting Ligands. Angiogenesis targeting refers to the use of an agent to bind to neovascular tissue. Tumor angiogenesis targeting refers to the use of an agent to bind to tumor neovascularization and tumor cells. Agents that are used for this purpose are known to those of ordinary skill in the art for use in performing various tumor measurements, including measurement of the size of a tumor vascular bed, and measurement of tumor volume. Some of these agents bind to the vascular wall. One of ordinary skill in the art would be familiar with the agents that are available for use for this purpose. Non-limiting examples of angiogenesis targeting ligands include celecoxib, C225, herceptin, angiostatin, and thalidomide, which have been developed for the assessment of biochemical process on angiogenesis.

In certain embodiments, a tumor targeting ligand may associate with tumor tissues by targeting the hypoxia associated with tumor cells. Examples of tumor targeting ligands that target hypoxic tissues include nitroimidazole and metronidazole, and these ligands may also be used to target other hypoxic tissues that are hypoxic due to a reason other than cancer (e.g., stroke).

Apoptosis Targeting Ligands. Apoptosis targeting refers to the use of an agent to bind to a cell that is undergoing apoptosis or is at risk of undergoing apoptosis. These agents are generally used to provide an indicator of the extent or risk of apoptosis, or programmed cell death, in a population of cells, such as a tumor. One of ordinary skill in the art would be familiar with agents that are used for this purpose. An "apoptosis targeting ligand" is a ligand that is capable of performing "apoptosis targeting" as defined in this paragraph. An example of a tumor apoptosis targeting ligand includes TRAIL (TNF-related apoptosis inducing ligand) monoclonal antibody. Other examples of apoptosis targeting ligands include a substrate of caspase-3, such as peptide or polypeptide that includes the 4 amino acid sequence aspartic acid-glutamic acid-valine-aspartic acid (for example, a peptide or chelator that includes the amino acid sequence aspartic acid-glutamic acid-valine-aspartic acid), and any member of the Bcl family. Examples of Bcl family members include, for example, Bax, Bcl-xL, Bid, Bad, Bak and Bcl-2. One of ordinary skill in the art would be familiar with the Bcl family, and their respective substrates.

Disease Receptor Targeting Ligands. As "disease receptor targeting ligands," certain agents are exploited for their ability to bind to certain cellular receptors that are overexpressed in disease states, such as cancer, neurological diseases and cardiovascular diseases. Examples of such receptors which are targeted include estrogen receptors, amino acid transporters, androgen receptors, pituitary receptors, transferrin receptors, progesterone receptors, and glucose transporters. Non-limiting examples of agents that can be applied as disease-receptor targeting ligands include androgen, estrogen, somatostatin, progesterone, transferrin, luteinizing hormone and luteinizing hormone antibody. Disease receptor targeting ligands (e.g., pentetreotide, octreotide, transferrin, and pituitary peptide) bind to cell receptors, some of which are overexpressed on certain cells.

Estrogen, estrone and tamoxifen target the estrogen receptor. Estrogen receptors are overexpressed in certain kinds of cancer, and conjugates that comprise an estrogen receptor targeting ligand may be used in certain embodiments to image tumors. The expression of estrogen receptors is also altered in the diseases of osteoporosis and endometriosis. It is anticipated that a conjugate comprising an estrogen receptor targeting ligand may be used to image other diseases such as osteoporosis and endometriosis.

Glucose transporters are overexpressed in various diseased cells such as certain cancerous cells. Tetraacetate mannose, deoxyglucose, certain polysaccharides (e.g., neomycin, kanamycin, tobramycin), and monosaccharides (e.g., glucosamine) also bind the glucose transporter and may be used as disease receptor targeting ligands. Since these ligands are not immunogenic and are cleared quickly from the plasma, receptor imaging would seem to be more promising compared to antibody imaging.

Similarly, amino acid transporters are also overexpressed in various diseased cells such as certain cancerous cells. Amino acids and/or amino acid derivatives (e.g., serine, tyrosine, alpha methyltyrosine) may be used as disease receptor targeting ligands.

Additional receptor targeting ligands are available and may be conjugated to polymer compounds. Other examples of disease receptor targeting ligands include leuteinizing hormone and transferrin. EGFR-TK expression and biologic correlation of specific receptor targeting in brain and other tissues. Diseases associated with changes in dopaminergic synthetic rate such as chemotoxin-induced neuron loss (MPTP, cocaine), drug-induced neurotoxicity (such as related to treatment with chemotherapy drugs), Parkinson's disease (PD), Huntington disease, dementia and cognition, psychosis, depression, schizophrenia, obesity and stem cell therapy follow-up.

The folate receptor is included herein as another example of a disease receptor. Folate receptors (FRs) are overexposed on many neoplastic cell types (e.g., lung, breast, ovarian, cervical, colorectal, nasopharyngeal, renal adenocarcinomas, malignant melanoma and ependymomas), but primarily expressed only several normal differentiated tissues (e.g., choroid plexus, placenta, thyroid and kidney). Examples of folate receptor targeting ligands include folic acid and analogs of folic acid. In certain embodiments, a folate receptor targeting ligand is selected from the group consisting of folate, folic acid, methotrexate and tomudex. Folic acid as well as antifolates such as methotrexate enter into cells via high affinity folate receptors (glycosylphosphatidylinositol-linked membrane folate-binding protein) in addition to classical reduced-folate carrier system.

Tumor Targeting Ligands. "Tumor targeting" refers to the ability of a compound to preferentially associate with tumors (e.g., cancerous, pre-cancerous, benign). A "tumor targeting ligand" refers to a compound which preferentially binds to or associates with tumor tissues, as compared to non-tumor tissues. Ligands (e.g., small molecules or antibodies) which preferentially target tumors are well known in the art, and it is anticipated that tumor targeting ligands that are currently known, or which may be subsequently discovered, may be used with the present invention. Disease receptor targeting refers to the ability of a compound to preferentially associate with receptors whose altered expression correlates with presence of a disease. For example, disease receptor targeting can be used to treat diseases associated with altered dopaminergic synthetic rate.

Disease Cell Cycle Targeting Ligands. Disease cell cycle targeting refers to the targeting of agents that are upregulated in proliferating cells. Compounds used for this purpose can be used to measure various parameters in cells, such as tumor cell DNA content. Certain disease cell cycle targeting ligands are nucleoside analogues. For example, pyrimidine nucleoside (e.g., 2'-fluoro-2'-deoxy-5-iodo-β-D-arabinofuranosyluracil [FIAU], 2'-fluoro-2'-deoxy-5-iodo-1-β-D-ribofuranosyl-uracil [FIRU], 2'-fluoro-2'-5-methyl-β-D-arabinofuranosyluracil [FMAU], 2'-fluoro-2'-deoxy-5-iodovinyl-1-β-D-ribofuranosyluracil [IVFRU]) and acycloguanosine: 9-[(2-hydroxy-1-(hydroxymethyl)ethoxy)methyl]guanine (GCV) and 9-[4-hydroxy-3-(hydroxymethyl)butyl]guanine (PCV) and other 18F-labeled acycloguanosine analogs, such as 8-fluoro-9-[(2-hydroxy-1-(hydroxymethyl)ethoxy)methyl] guanine (FGCV), 8-fluoro-9-[4-hydroxy-3-(hydroxymethyl)butyl]guanine (FPCV), 9-[3-fluoro-1-hydroxy-2-propoxy methyl]guanine (FHPG), and 9-[4-fluoro-3-(hydroxymethyl)butyl]guanine (FHBG) have been developed as reporter substrates for imaging wild-type and mutant HSV1-tk expression. One of ordinary skill in the art would be familiar with these and other agents that are used for disease cell cycle targeting.

Examples of disease targeting ligands include, for example, adenosine and penciclovir. The antiviral nucleoside analog FHBG (a penciclovir analog), another disease targeting ligand, has for in vivo measurement of cell proliferation using PET, and it is anticipated that similar targeting ligands may be used with the present invention.

Hypoxia Targeting Ligands. Hypoxia targeting refers to the targeting of agents that are upregulated in hypoxic cells. Compounds used for this purpose can be used to measure various parameters in cells, such as tumor cell hypoxia, resistance or residual content. In some embodiments of the present invention, the targeting ligand is a tumor hypoxia targeting ligand. For example, tumor cells are more sensitive to conventional radiation in the presence of oxygen than in its absence; even a small percentage of hypoxic cells within a tumor could limit the response to radiation. Hypoxic radioresistance has been demonstrated in many animal tumors but only in few tumor types in humans. Examples of tumor hypoxia targeting ligands include annexin V, colchicine, nitroimidazole, mitomycin and metronidazole.

Detectable moieties. Examples of directly detectable entities (or signaling moieties) that can be ligands or coupled to ligands include radioisotopes, fluorophores, dyes, enzymes, nanoparticles, colored latex particles, chemiluminescent markers, light-emitting dyes, and others described herein and known in the art.

Radioisotopes can be used as directly detectable entities include 32P, 33P, 35S, 3H, and 1251. These radioisotopes have different half-lives, types of decay, and levels of energy which can be tailored to match the needs of a particular protocol.

Fluorophores or fluorochromes that can be used as directly detectable entities include fluorescein, tetramethylrhodamine, Texas Red, and a number of others (e.g., Haugland, Handbook of Fluorescent Probes-9th Ed., 2002, Molec. Probes, Inc., Eugene Oreg.; Haugland, The Handbook: A Guide to Fluorescent Probes and Labeling Technologies-10th Ed., 2005, Invitrogen, Carlsbad, Calif.). Also included are light-emitting or otherwise detectable dyes. The light emitted by the dyes can be visible light or invisible light, such as ultraviolet or infrared light. In exemplary embodiments, the dye may be a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-(ε-carboxypentyl)-3-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4',5-dichloro-2',7-dimethoxyfluorescein (JOE); ALEXA FLUOR; Cy2; Texas Red and Rhodamine Red; 6-carboxy-2',4,7,7'-tetrachlorofluorescein (TET); 6-carboxy-2',4,4',5',7,7-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; IR800CW, ICG, Alexa Fluor 350; Alexa Fluor 488; Alexa Fluor 532; Alexa Fluor 546; Alexa Fluor 568; Alexa Fluor 594; Alexa Fluor 647; Alexa Fluor 680, or Alexa Fluor 750.

Very small particles, termed nanoparticles, also can be used as directly detectable entities. These particles usually range from 1-1000 nm in size and include diverse chemical structures such as gold and silver particles and quantum dots. When irradiated with angled incident white light, silver or gold nanoparticles ranging from about 40-120 nm will scatter monochromatic light with high intensity. The wavelength of the scattered light is dependent on the size of the particle. Four to five different particles in close proximity will each scatter monochromatic light, which when superimposed will give a specific, unique color. Derivatized nanoparticles such as silver or gold particles can be attached to a broad array of molecules including, proteins, antibodies, small molecules, receptor ligands, and nucleic acids. Specific examples of nanoparticles include metallic nanoparticles and metallic nanoshells such as gold particles, silver particles, copper particles, platinum particles, cadmium particles, composite particles, gold hollow spheres, gold-coated silica nanoshells, and silica-coated gold shells. Also included are silica, latex, polystyrene, polycarbonate, polyacrylate, PVDF nanoparticles, and colored particles of any of these materials.

B. Linkers

The polymers of the present invention can also incorporate any suitable linker L. The linkers provide for attachment of the ligands to the polymer. The linkers can be cleavable or non-cleavable, homobifunctional or heterobifunctional. Other linkers can be both heterobifunctional and cleavable, or homobifunctional and cleavable. "Linker" refers to a chemical moiety that links two groups together. The linker can be cleavable or non-cleavable. Cleavable linkers can be hydrolyzable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a ligand.

Cleavable linkers include those that are hydrolyzable linkers, enzymatically cleavable linkers, pH sensitive linkers, disulfide linkers and photolabile linkers, among others. Hydrolyzable linkers include those that have an ester, carbonate or carbamate functional group in the linker such that reaction with water cleaves the linker. Enzymatically cleavable linkers include those that are cleaved by enzymes and can include an ester, amide, or carbamate functional group in the linker. pH sensitive linkers include those that are stable at one pH but are labile at another pH. For pH sensitive linkers, the change in pH can be from acidic to basic conditions, from basic to acidic conditions, from mildly acidic to strongly acidic conditions, or from mildly basic to strongly basic conditions. Suitable pH sensitive linkers are known to one of skill in the art and include, but are not limited to, ketals, acetals, imines or imminiums, siloxanes, silazanes, silanes, maleamates-amide bonds, ortho esters, hydrazones, activated carboxylic acid derivatives and vinyl ethers. Disulfide linkers are characterized by having a disulfide bond in the linker and are cleaved under reducing conditions. Photolabile linkers include those that are cleaved upon exposure to light, such as visible, infrared, ultraviolet, or electromagnetic radiation at other wavelengths. Other linkers useful in the present invention include those described in U.S. Patent Application Nos. 2008/0241102 and 2008/0152661 Other linkers include those described in Bioconjugate Techniques, Greg T. Hermanson, Academic Press, 2d ed., 2008 (incorporated in its entirety herein), and those described in Angew. Chem. Int. Ed. 2009, 48, 6974-6998, incorporated in its entirety herein.

In some embodiments, linkers can have a length of up to 30 atoms, each atom independently C, N, O, S, and P. In other embodiments, the linkers can be any of the following: $-C_{1-12}$ alkyl-, $-C_{3-12}$ cycloalkyl-, $-(C_{1-8}$ alkyl)-($C_{3-12}$ cycloalkyl)-($C_{0-8}$ alkyl)-, $-(CH_2)_{1-12}O-$, $(-(CH_2)_{1-6}-O-(CH_2)_{1-6}-)_{1-12}-$, $(-(CH_2)_{1-4}-NH-(CH_2)_{1-4})_{1-12}-$, $(-(CH)_{1-4}-O-(CH_2)_{1-4})_{1-12}-O-$, $(-(CH_2)_{1-4}-O-(CH_2)_{1-4}-)_{1-12}-O-(CH_2)_{1-12}-$, $-(CH_2)_{1-12}-(C{=}O)-O-$, $-(CH_2)_{1-12}-O-(C{=}O)-$, -(phenyl)-$(CH_2)_{1-3}-(C{=}O)-O-$, -(phenyl)-$(CH_2)_{1-3}-$ (C)—NH—, —($C_{1-6}$ alkyl)-(C═O)—O—($C_{0-6}$ —$(CH_2)_{1-12}$—(C)—O—$(CH_2)_{1-12}$—, —CH(OH)—CH (OH)—(C═O)—O—CH(OH)—CH(OH)—(C)—NH—, —S-maleimido-$(CH_2)_{1-6}$—, —S-maleimido-($C_{1-3}$ alkyl)-(C═O)—NH—, —S-maleimido-($C_{1-3}$ alkyl)-($C_{5-6}$ cycloalkyl)-($C_{0-3}$ alkyl)-, —($C_{1-3}$ alkyl)-($C_{5-6}$ cycloalkyl)-($C_{0-3}$ alkyl)-(C═O)—O—, —($C_{1-3}$ alkyl)-($C_{5-6}$ cycloalkyl)-($C_{0-3}$ alkyl)-(C═O)—NH—, —S-maleimido-($C_{0-3}$ alkyl)-phenyl-($C_{0-3}$ alkyl)-, —($C_{0-3}$ alkyl)-phenyl-(C═O)—NH—, —$(CH_2)_{1-12}$—NH—(C═O)—, —$(CH_2)_{1-12}$—(C═O)—NH—, -(phenyl)-$(CH_2)_{1-3}$—(C═O)—NH—, —S—$(CH_2)$—(C)—NH-(phenyl)-, —$(CH_2)_{1-12}$—(C═O)—NH—$(CH_2)_{1-12}$—, —$(CH_2)_2$—(C═O)—O—$(CH_2)_2$—O—(C═O)—$(CH_2)_2$—(C═O)—NH—, —($C_{1-6}$ alkyl)-(C═O)—N—($C_{1-6}$ alkyl)-, acetal, ketal, acyloxyalkyl ether, —N═CH—, —($C_{1-6}$ alkyl)-S—S—($C_{0-6}$ alkyl)-, —($C_{1-6}$ alkyl)-S—S—($C_{1-6}$ alkyl)-(C═O)—O—, —($C_{1-6}$ alkyl)-S—S—($C_{1-6}$ alkyl)-(C═O)—NH—, —S—S—$(CH_2)_{1-3}$—(C═O)—NH—$(CH_2)_{1-4}$—NH—(C)— $(CH_2)_{1-3}$—, —S—S—($C_{0-3}$ alkyl)-(phenyl)-, —S—S—($C_{1-3}$ alkyl)-(phenyl)-(C═O)—NH—$(CH_2)_{1-5}$—, —($C_{1-3}$ alkyl)-(phenyl)-(C═O)—NH—$(CH_2)_{1-5}$—(C)—NH—, —S—S—($C_{1-3}$ alkyl)-, —($C_{1-3}$ alkyl)-(phenyl)-(C═O)—NH—, —O—($C_{1-6}$ alkyl)-S($O_2$)—($C_{1-6}$ alkyl)-O—(C═O)—NH—, —S—S—$(CH_2)_{1-3}$—(C)—, —$(CH_2)_{1-3}$—(C)—NH—N═C—S—S—$(CH_2)_{1-3}$—(C═O)—NH —$(CH_2)_{1-5}$—, —$(CH_2)_{1-3}$—(C)—NH—$(CH_2)_{1-5}$—(C═O)—NH—, —$(CH_2)_{0-3}$-(heteroaryl)-$(CH_2)_{0-3}$—, —$(CH_2)_{0-3}$-phenyl-$(CH_2)_{0-3}$—, —N═C(R)—, —($C_{1-6}$ alkyl)-C(R)═N—($C_{1-6}$ alkyl)-, —($C_{1-6}$ alkyl)-(aryl)-C(R) ═N—($C_{1-6}$ alkyl)-, —($C_{1-6}$ alkyl)-C(R)═N-(aryl)-($C_{1-6}$ alkyl)-, and —($C_{1-6}$ alkyl)-O—P(O)(OH)—O—($C_{0-6}$ alkyl)-, wherein R is H, $C_{1-6}$ alkyl, $C_{3-6}$ cycloalkyl, or an aryl group having 5-8 endocyclic atoms.

In some other embodiments, linkers can be any of the following: —$C_{1-12}$ alkyl-, —$C_{3-12}$ cycloalkyl-, (—$(CH_2)_{1-6}$—O—$(CH_2)_{1-6}$—$)_{1-12}$—, (—$(CH_2)_{1-4}$—NH—$(CH_2)_{1-4})_{1-12}$—, —$(CH_2)_{1-12}$—O—, (—$(CH_2)_{1-4}$—O—$(CH_2)_{1-4})_{1-12}$—O—, —$(CH_2)_{1-12}$—(CO)—O—, —$(CH_2)_{1-12}$—(CO)—NH—, —$(CH_2)_{1-12}$—O—(CO)—, —$(CH_2)_{1-12}$—NH— (CO)—, (—$(CH_2)_{1-4}$—O—$(CH_2)_{1-4})_{1-12}$—O— $(CH_2)_{1-12}$—, —$(CH_2)_{1-12}$—(CO)—O—$(CH_2)_{1-12}$—, —$(CH_2)_{1-12}$—(CO)—NH—$(CH_2)_{1-12}$—, —$(CH_2)_{1-12}$—O—(CO)—$(CH_2)_{1-12}$—, —$(CH_2)_{1-12}$—NH—(CO)—$(CH_2)_{1-12}$—, —($C_{3-12}$ cycloalkyl)-, —($C_{1-8}$ alkyl)-($C_{3-12}$ cycloalkyl)-, —($C_{3-12}$ cycloalkyl)-($C_{1-8}$alkyl)-, —($C_{1-8}$alkyl)-($C_{3-12}$ cycloalkyl)-($C_{1-8}$alkyl)-, and —$(CH_2)_{0-3}$-aryl-$(CH_2)_{0-3}$—.

In still other embodiments, a linker is a cleavable linker independently selected from hydrolyzable linkers, enzymatically cleavable linkers, pH sensitive linkers, disulfide linkers and photolabile linkers.

"Hydrolyzable linker" refers to a chemical linkage or bond, such as a covalent bond, that undergoes hydrolysis under physiological conditions. The tendency of a bond to hydrolyze may depend not only on the general type of linkage connecting two central atoms between which the bond is severed, but also on the substituents attached to these central atoms. Non-limiting examples of hydrolytically susceptible linkages include esters of carboxylic acids, phosphate esters, acetals, ketals, acyloxyalkyl ether, imines, orthoesters, and some amide linkages.

"Enzymatically cleavable linker" refers to a linkage that is subject to degradation by one or more enzymes. Some hydrolytically susceptible linkages may also be enzymatically degradable. For example, esterases may act on esters of carboxylic acid or phosphate esters, and proteases may act on peptide bonds and some amide linkages.

"pH sensitive linker" refers to a linkage that is stable at one pH and subject to degradation at another pH. For example, the pH sensitive linker can be stable at neutral or basic conditions, but labile at mildly acidic conditions.

"Photolabile linker" refers to a linkage, such as a covalent bond, that cleaves upon exposure to light. The photolabile linker includes an aromatic moiety in order to absorb the incoming light, which then triggers a rearrangement of the bonds in order to cleave the two groups linked by the photolabile linker.

III. APPLICATIONS

Functionalized water-soluble conjugated polymers described herein can be employed in a range of applications including therapy, sensing, bioimaging, and/or flow cytometry analysis.

A. Therapy

Water-soluble conjugated polymers described herein can be used in conjunction with methods of treating subjects with various diseases, such as cancer. A therapeutic method can comprise administering an appropriate conjugated polymer to a subject in need of such therapy.

B. Sensing

Water-soluble conjugated polymers described herein can be used in conjunction with analytical methods comprising contacting a sample with an appropriate conjugated polymer and detecting a change in the properties of the conjugated polymers as a basis for sensing changes in the sample under certain conditions.

C. Bioimaging

Water-soluble conjugated polymers described herein can be used in conjunction with methods of cellular imaging comprising contacting target cells with an appropriate conjugated polymer and detecting cellular imaging. In one embodiment, the target cells are cancer cells or cells that preferentially accumulate in tumors. Imaging can be in vitro imaging or in vivo imaging. Imaging methods can be used for diagnosing a tumor or cancer through in vivo cellular imaging. In vivo cellular imaging can be conducted using non-invasive live animal fluorescence imaging techniques. In certain aspects the in vitro imaging can be in the context of flow cytometric analysis.

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Bio-Functionalization of Water-Soluble Poly(Phenylene Ethynylene)S

Taking advantage of the amidation reaction, a platform was developed for post-polymerization functionalization of a water-soluble poly(phenylene ethynylene) (PPE) type conjugated polyelectrolyte. Herein the strategy by synthesis of PPEs that are functionalized with five different bio- or photo-active functional groups in a controlled manner in aqueous solution is demonstrated (Scheme I). The precursor PPE is an alternating co-polymer featuring carboxylate (—R—COO—) and sulfonate (—R—$SO_3$—) solubilizing groups. The carboxylate groups are activated with appropriate reagents and react with various amine-containing molecules giving rise to the functional polymers. The sulfonate groups in the side-chains give rise to good water solubility of the resulting functionalized conjugated polyelectrolytes. In this study we have determined optimized reaction conditions for the amidation reaction, and then utilized the method to prepare a family of five functionalized PPE-type conjugated polyelectrolytes. Conjugated polyelectrolytes modified with rhodamine and biotin were further studied with respect to their pH response and in an example flow cytometry study of biotin-avidin recognition. This work enables the facile introduction of a variety of functional groups on water-soluble conjugated polymers, which allows creation of new materials with diverse applications in biosensing, diagnostics and therapy.

Scheme 1. Functionalization of PPE

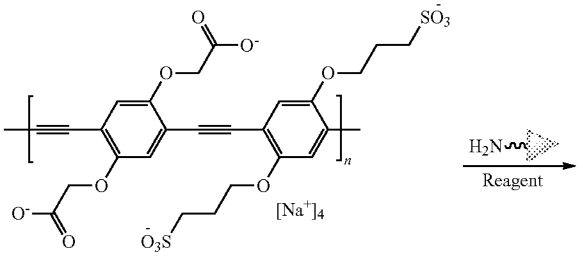

PPE

-continued

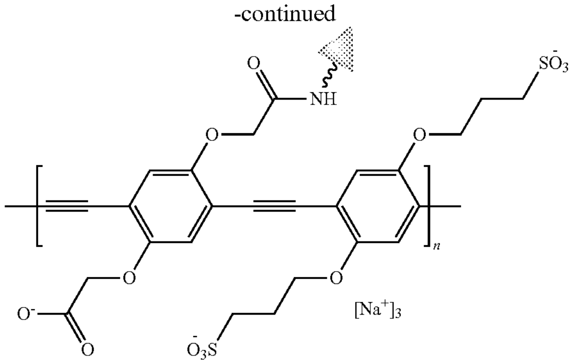

PPE derivatives

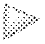 = Functional groups

Polymer Derivatization. The synthesis of water-soluble PPE is outlined in Scheme 2. An AA/BB type polymerization under Sonogashira conditions of monomers 1 and 2 afforded the conjugated polymer PPE-ester in a 67% yield with a number average molecular weight (Mn) of 16,000 and a polydispersity index (D=Mw/Mn) of 2.1 determined by gel permeation chromatography analysis. The number average degree of polymerization is 16 (there are two phenylene ethynylene units per repeat). The water-soluble polymer PPE was obtained by base-promoted hydrolysis of PPE-ester carried out in a mixed 1,4-dioxane/water solution in a 95% yield. With the R—$SO_3$— and R—$CO_2$— groups on the sidechains, PPE was readily soluble in water at room temperature. The UV-visible absorption spectrum of PPE in water features a maximum at 434 nm with a molar absorption coefficient of $3.6\times10^4$ $L\cdot mol^{-1}\cdot cm^{-1}$ and the fluorescence spectrum exhibits a maximum at 460 nm in water with an absolute fluorescence quantum yield of 19%.

Scheme 2. Synthetic route to PPE

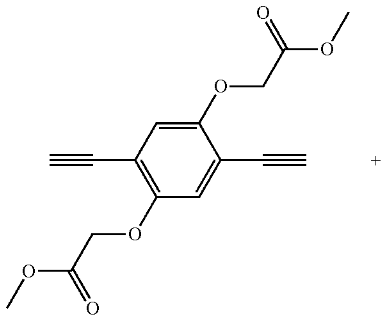

1

-continued

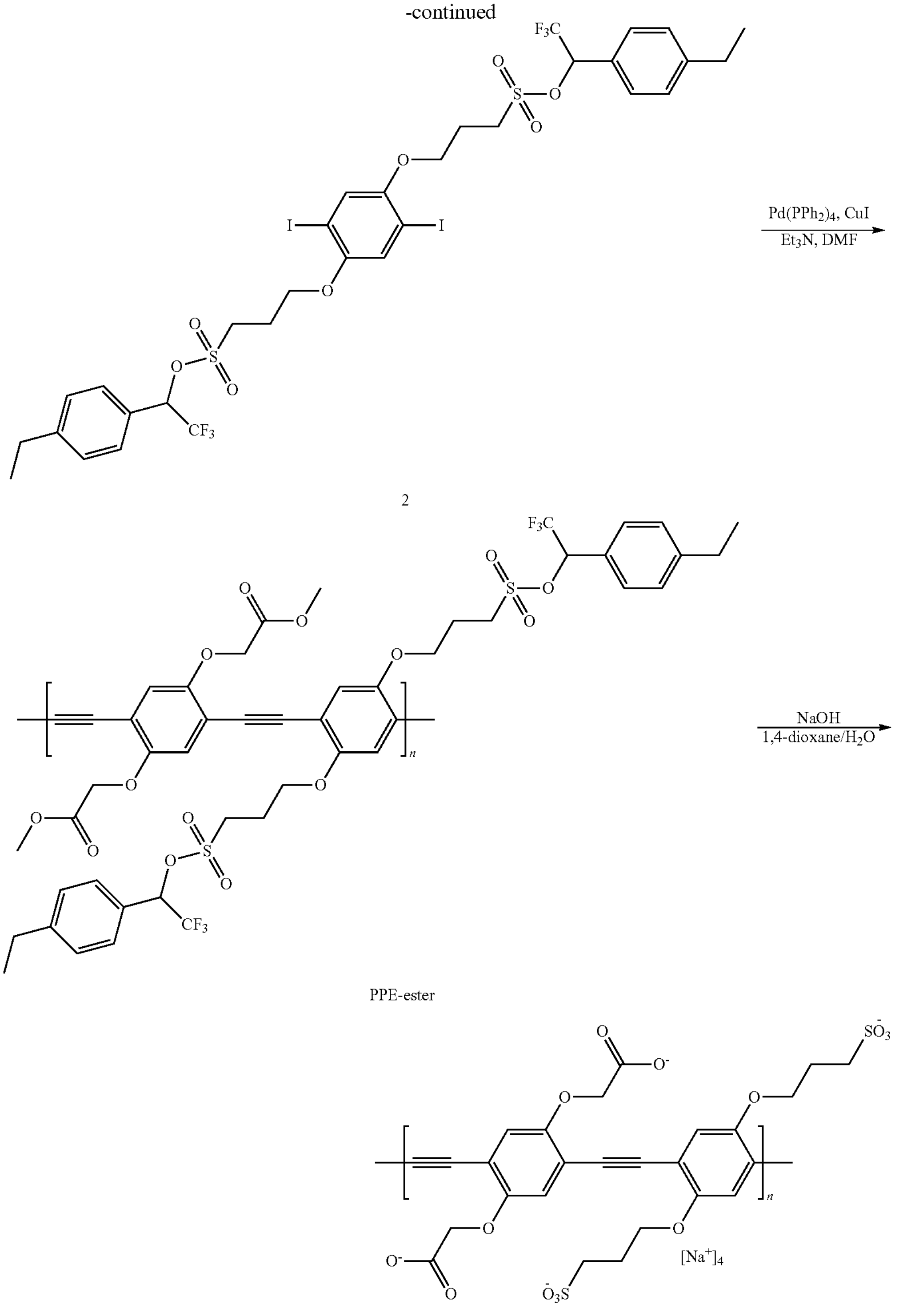

PPE

Coupling of PPE with biotin-ethylenediamine (Biotin-EDA, Scheme 3) was employed as a model reaction for optimization studies. Biotin was selected as the initial bio-functional group, given that it has an extraordinarily high affinity to avidin, and has been widely used in proteomics, assembly, detection, labeling and drug delivery.[27-30] A variety of coupling reagents and reaction conditions were used to explore the efficiency of the coupling reactions. Aminium salts (HATU, HBTU) and a carbodiimide (EDCI) with different promoters (DMAP, HOBT, NHS) were assessed as coupling reagents (Table 1, see footnote for acronyms). After each reaction, the product solution was diluted with water and dialyzed for 2 days to remove the small molecules and reaction by products. The extent of reaction of the available carboxyl units (m %) was assessed by analysis of the $^{1}$H NMR of the derivatized polymer. (Note that m=50% corresponds to on average one biofunctional group added per repeat unit). Most of the conditions afforded amidation except for EDCI and EDCl/DMAP in aqueous solution. The amidation reaction using EDCl/NHS as coupling reagents exhibited the highest m values (Table 1). The reaction conditions were further optimized by performing the EDCl/NHS amidation in different buffered aqueous solutions and the results found that reaction in MES buffer with a tunable pH (see Table 1) achieved the highest loading amount, m=53%, corresponding to just over one biotin per repeat unit. This may be because that a relatively low pH value is beneficial for the formation of the NHS ester in step I, and in step II, the pH was tuned to 8 after Biotin-EDA was added, and the resulting slightly basic medium is beneficial for the nucleophilic addition of Biotin-EDA with the NHS ester.

Scheme 3. Synthesis of PPE-biotin

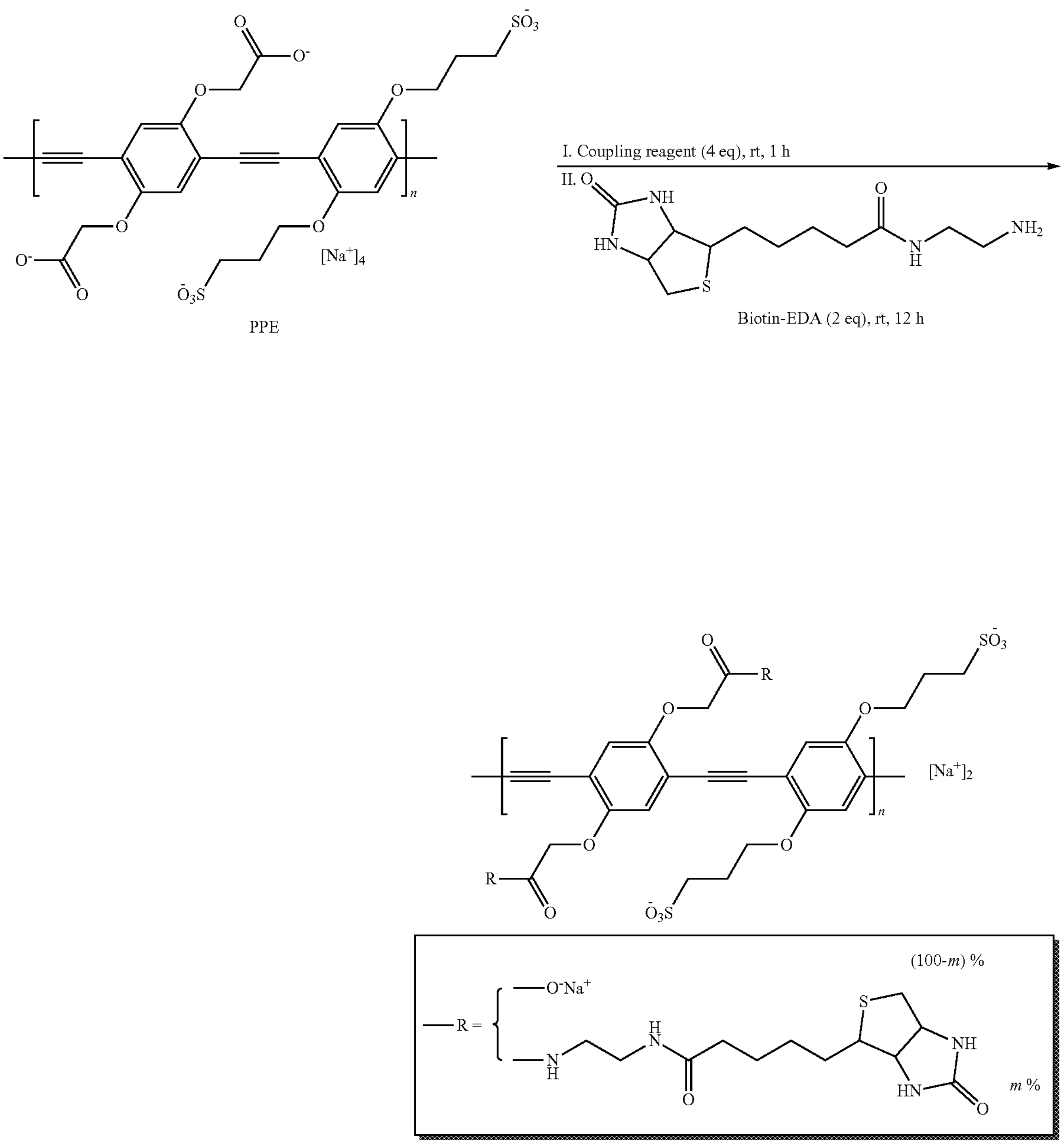

PPE-biotin

TABLE 1

| Screening of Reaction Conditions | | | |
|---|---|---|---|
| entry | coupling reagent [a] | solvent | % loading (m) |
| 1 | HBTU, $^{i}Pr_2NEt$ | $H_2O$/DMF | 15 |
| 2 | HATU, $^{i}Pr_2NEt$ | $H_2O$/DMF | 22 |
| 3 | EDCI | $H_2O$ | 0 |
| 4 | EDCI, DMAP | $H_2O$ | 0 |
| 5 | EDCI, HOBT | $H_2O$ | 7 |
| 6 | EDCI, NHS | $H_2O$ | 37 |
| 7 | EDCI, NHS | PBS | 31 |
| 8 | EDCI, NHS | MES [b] | 53 |

[a] HBTU = 1-[(dimethylamino)(dimethyliminio)methyl]-1H-benzo[d][1,2,3]triazole 3-oxide hexafluorophosphate, HATU = 1-((dimethylamino)(dimethyliminio)methyl)-1H-[1,2,3]triazolo[4,5-b]pyridine 3-oxide hexafluorophosphate, EDCI = 1-ethyl-3-(3-dimethylaminopropyl)carbodiimide hydrochloride, DMAP = 4-dimethylaminopyridine, HOBT = 1-hydroxybenzotriazole, NHS = N-hydroxysuccinimide.

[b] In step I, the pH value of MES buffer is 5. In step II, after adding biotin-EDA, the pH of MES buffer is tuned to 8 by adding NaOH solution.

Figure 1:
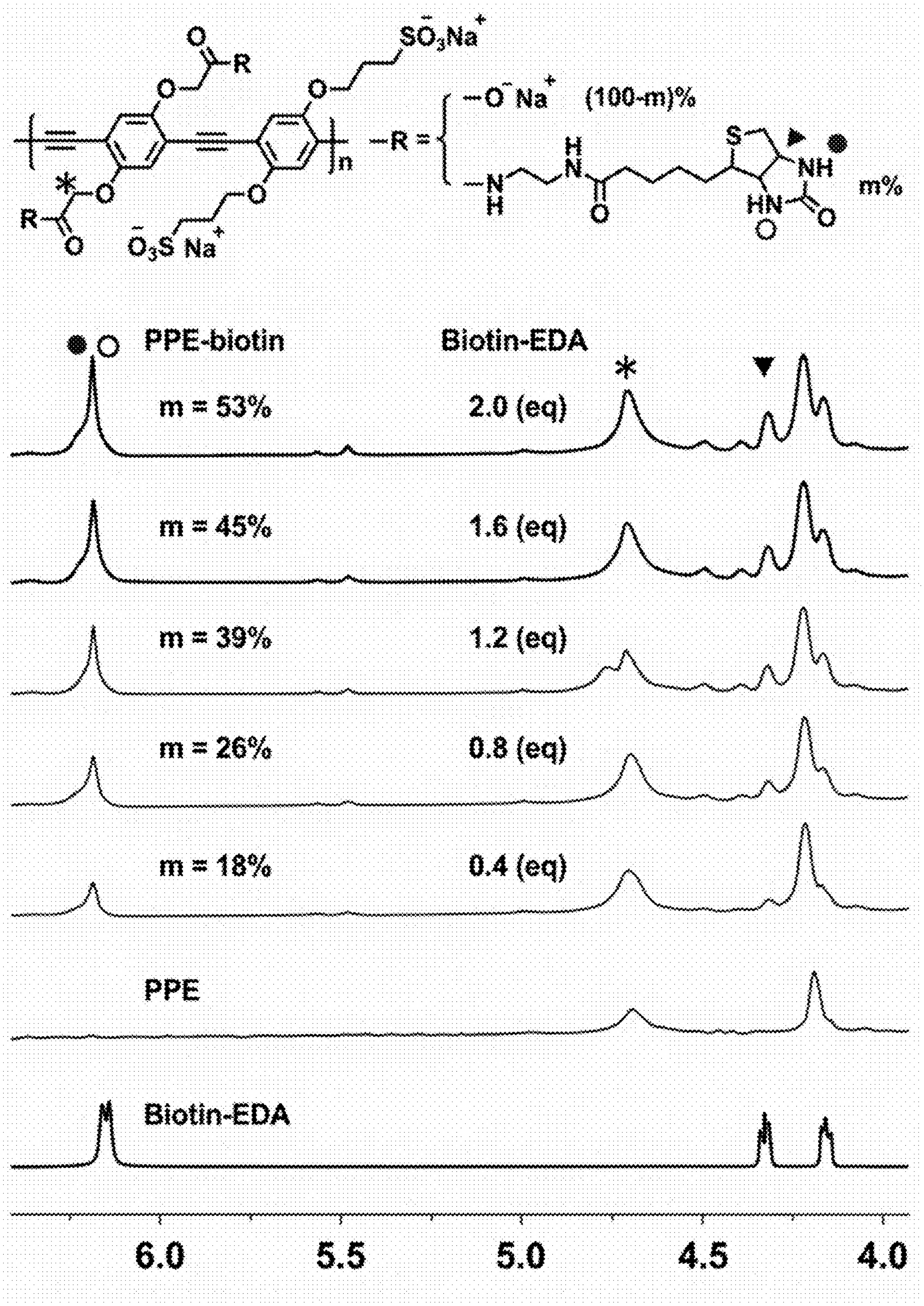
FIG. 1. Analysis of the loading of biotin onto PPE. The $^1H$ NMR was performed at 75° C. in DMSO-d6.

In order to test if Biotin-EDA could be introduced onto the PPE side-chains with control over the degree of functionalization (m %), five separate reactions were performed under the same reaction conditions with varying molar equivalents (0.4, 0.8, 1.2, 1.6, and 2.0) of biotin relative to the concentration of the PPE repeat units. The $^1$H NMR spectra demonstrated the coupling of biotin onto PPE and allowed quantification of the degree of functionalization. In particular, as shown in FIG. 1, the methine protons signals (δ 4.32 ppm) on biotin were clearly observed in the spectra of PPE-Biotin. Integration of these peaks relative the signals of the protons from the methylene unit adjacent to the PPE carboxylate units (δ 4.71 ppm) established the degree of biotin functionalization. As the number of equivalents of biotin used in the reaction increased, the loading amount of biotin increased from m=18% to m=53%, corresponding to approximately 1 biotin per 3 repeat units, to just over 1 biotin per repeat. This result clearly shows that it is possible to vary the loading of the biofunctional group on the polymer scaffold in a controlled manner by varying the reaction stoichiometry.

Figure 5:
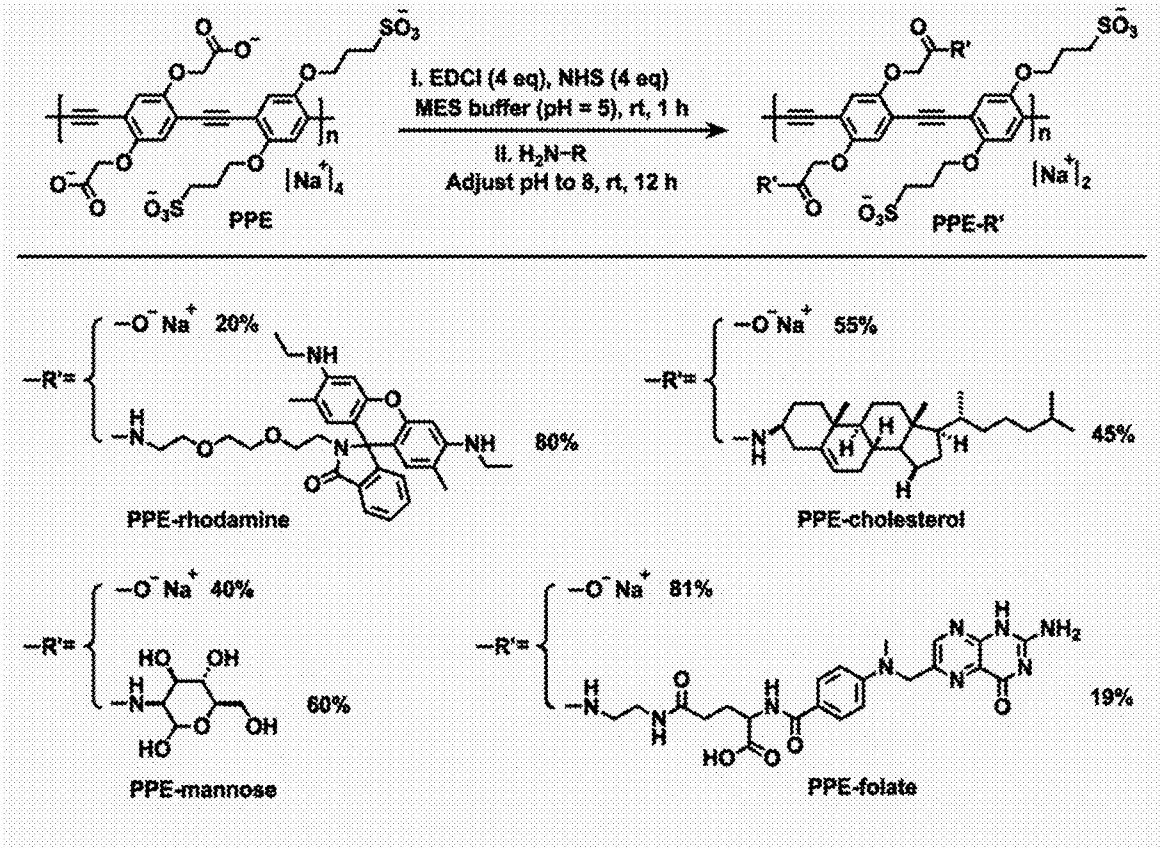
FIG. 5. Illustration of the versatility of the developed functionalization method. 2 eq Rhodamine-$NH_2$, 1.2 eq Cholesterol-NH), 2 eq Mannose-$NH_2$, 0.8 eq Folate-$NH_2$. (The stoichiometry of the molecules was varied in order to obtain good water solubility of PPE-R').
Figure 6:
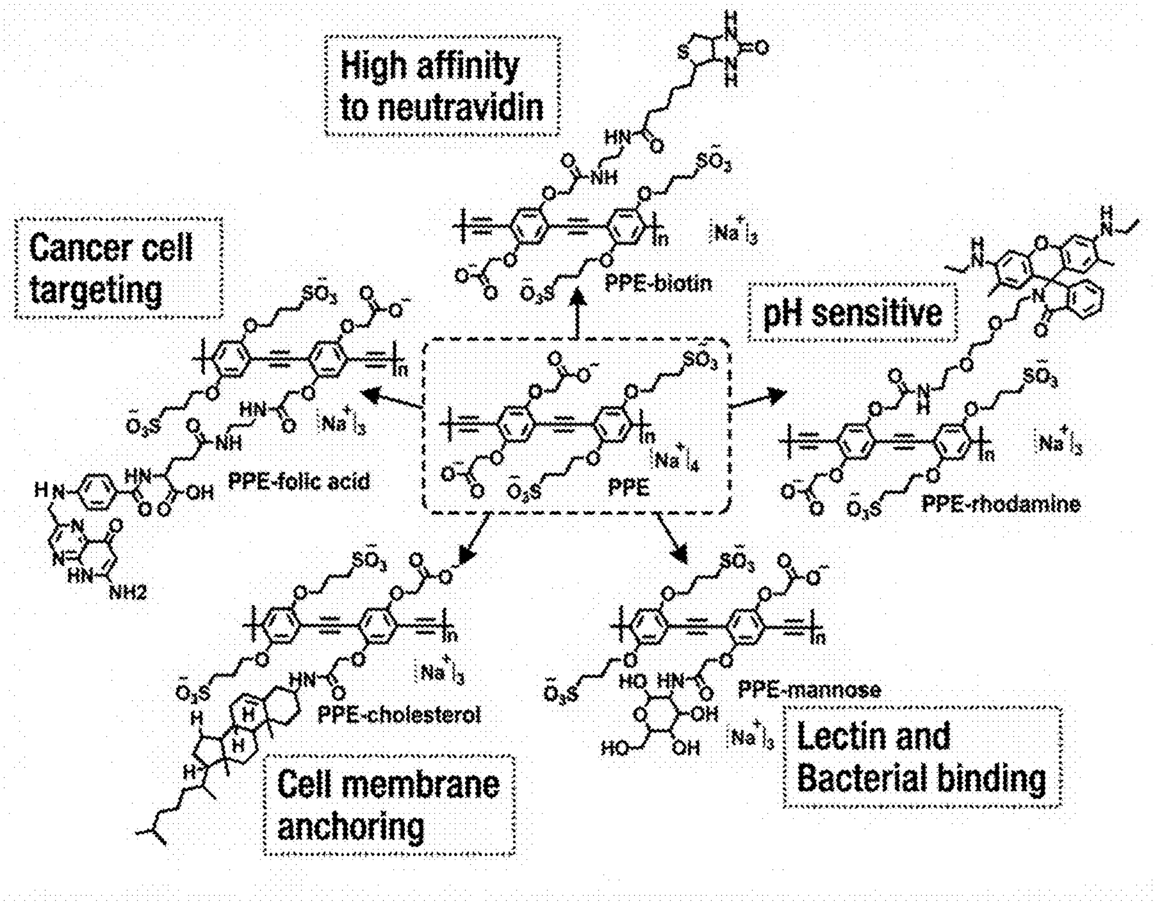
FIG. 6. Summarizes example applications of the compositions.

Having established the utility of the amidation reaction of PPE with Biotin-EDA, the versatility of this post-polymerization method were investigated by introducing several other different functional molecules. As shown in FIG. 5, rhodamine, folic acid, mannose, and cholesterol were employed to functionalize PPE. The loading level (m %) of these functional groups were determined from the $^1$H NMR spectra of the derivatized polymers. Four novel functionalized PPE derivatives were prepared by using the developed method, demonstrating the versatility of both PPE based platform and the post-polymerization functionalization reaction. The ability to prepare such functionalized, water-soluble conjugated polyelectrolytes in a straight-forward manner with good control of the loading level of functional molecules is desirable for many applications. For example, PPE-biotin could be used as fluorescence label for recognizing biotin binding proteins,[12] PPE-rhodamine could serve as a pH sensor (vide infra) and PPE-folic acid could selectively bind to a series of cancer cells for cell imaging and photodynamic therapy.[16-31] Finally, PPE-cholesterol could be used for cell membrane anchoring and PPE-mannose could bind to lectin and specific bacteria for antibacterial studies.[32,33]

Figures 2A, 2B, 2C:
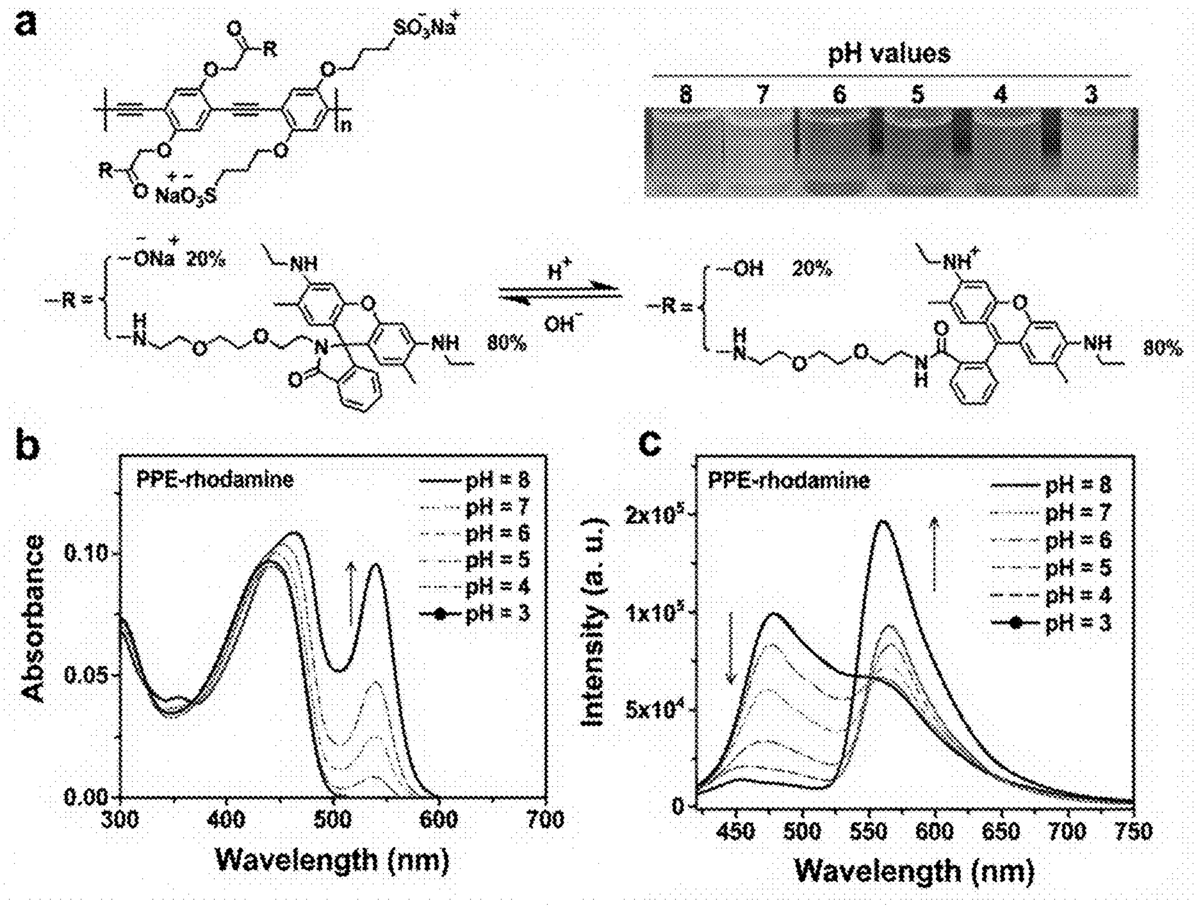
FIG. 2*a*-2*c*. (a) The structure conversion of PPE-rhodamine in basic and acidic conditions and the changes of emission colors from blue to pink as the pH values decrease from 8 to 3. (b) The absorption and (c) emission spectra of PPE-rhodamine in different pH values. The excitation wavelength was 360 nm. The concentration of PPE-rhodamine is 5 μM, the solvent is citrate-phosphate buffer.

Applications. To provide examples of the utility of the functionalized conjugated polyelectrolytes, PPE-rhodamine and PPE-biotin were used in preliminary work to investigate the applications. First, fluorescence studies of PPE-rhodamine were carried out to determine whether energy transfer occurred from the PPE backbone to the rhodamine side-groups. However, in carrying out this work, it was discovered that an interesting pH dependence of the optical spectra, which is primarily associated with the combined effects of pH on the rhodamine structure and a consequent effect on energy transfer from PPE to rhodamine. First, as shown in FIG. 2*a*, the rhodamine chromophore exists in two forms: (1) a spirolactam that is colorless and nonfluorescent is predominant at high pH; (2) a ring-opened form that absorbs in the mid-visible and is strongly fluorescent at low pH.[34] This effect is well-known and has been used to develop colorimetric and fluorescence-based sensors for a variety of applications including intracellular pH sensing.[35,36] As shown in FIG. 2*c*, as pH is decreased from 8 to 3, the absorption and fluorescence of PPE-rhodamine undergo significant changes. In particular, at high pH the absorption is dominated by the PPE backbone which exhibits a single absorption at ~430 nm. As the pH decreases, a second band emerges at 540 nm which is due to the ring opened form of the rhodamine units. 37 More interestingly, the fluorescence undergoes significant changes with pH. At high pH, the fluorescence is dominated by the PPE fluorescence, with $_{Amax}$=480 nm; as the pH decreases, the PPE fluorescence is quenched and replaced by a fluorescence at 570 nm which is characteristic of the rhodamine chromophore. The quenching of the PPE emission signals the turn-on of energy transfer from the backbone to the covalently attached rhodamine chromophore, and it is confirmed by emission excitation spectra. The overall changes in the fluorescence lead to a pronounced change in the emission color from blue to pink over the pH range 8-3.

Taken together these results demonstrated that PPE-rhodamine is a sensitive pH probe in the pH range of 8 to 3. The development of novel pH probe is important in biological research. The proton concentration in eukaryotic cells is unevenly distributed. For example, the cytoplasm is weakly alkaline, and its pH is around 7.2, while the pH in the lysosome is in the range of 6.0-4.0. The interior of endosomes and autophagosomes is also an acidic environment, which is of great significance for biological processes including autophagy and apoptosis. Due to the high sensitivity to pH, PPE-rhodamine is expected to be used as a potential probe to track the pH distribution in cells in real time.

In a second line of work, the use of PPE-biotin as a fluorescent label to signal the avidin-biotin interaction was explored. PPE-biotin is anionic in phosphate-buffered saline (PBS, pH=7.4) due the presence of the R—$CO_2$— and R—$SO_3$ side-groups. To investigate the interaction of PPE-biotin with a biotin-binding protein, neutravidin (NA), a deglycosylated native avidin from egg whites, was employed because of its low isoelectric point (pI~6.3) which suppresses nonspecific electrostatic binding to the anionic polyelectrolyte. The loading of biotin on PPE-biotin used in this study was 53%, which means that each repeat unit of PPE-biotin has on average approximately one biotin unit. Thus, the concentration of PPE-biotin (as polymer repeat units) is approximately equal to the biotin concentration.

Figures 3A, 3B, 3C, 3D:
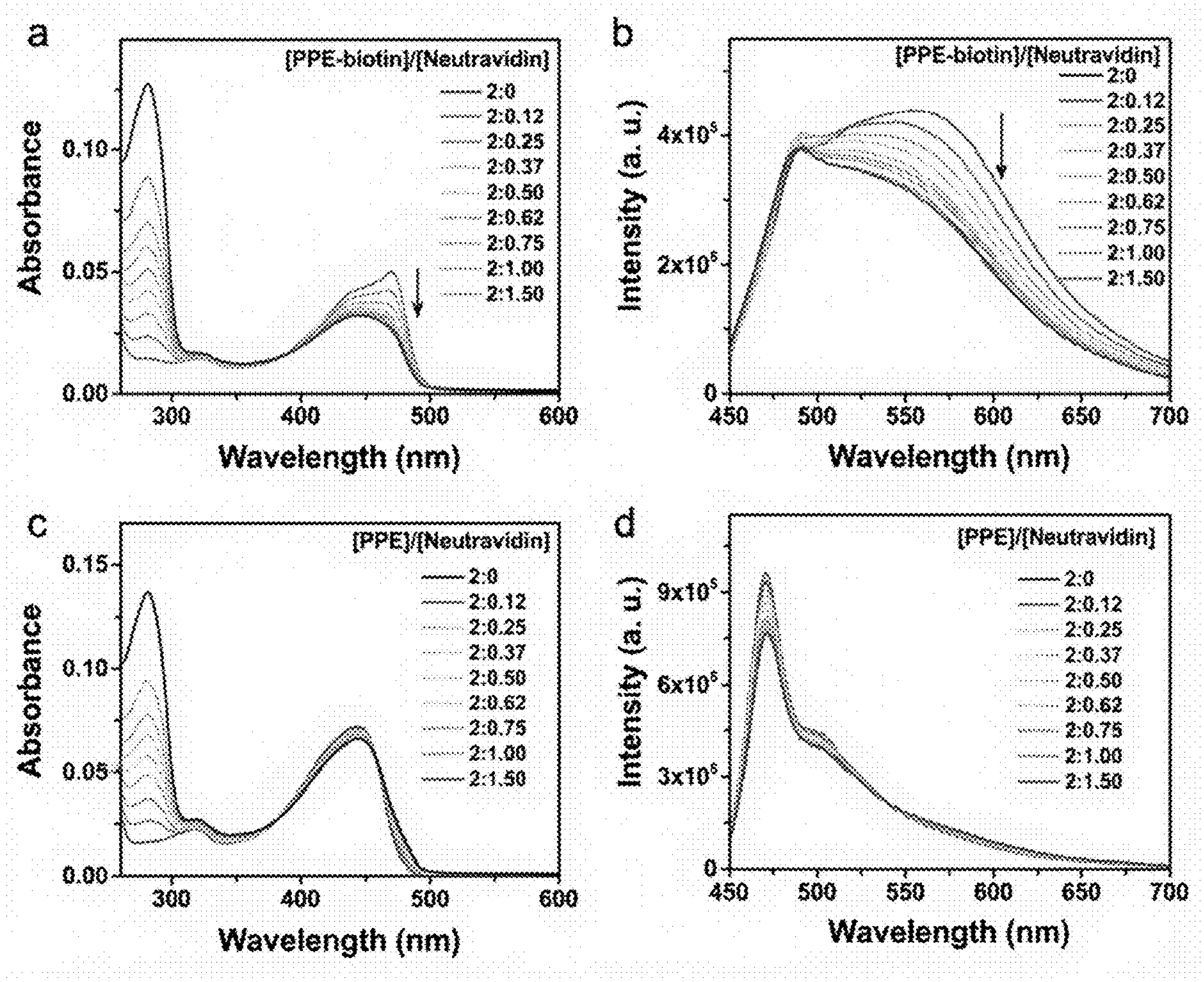
FIG. 3*a*-3*d*. UV-visible absorption and emission spectra of PPE-biotin (m=53%) (a, b) and PPE (c, d) with adding different concentration of neutravidin in PBS (containing 10% glycerol). The concentration of PPE-biotin and PPE was 2 μM. The concentrations of neutravidin increased from 0 to 1.50 μM (namely 0, 0.12, 0.25, 0.37, 0.5, 0.62, 0.75, 1.00, and 1.50 μM). The excitation wavelength was 440 nm.

As shown in FIG. 3*a*, the emission of PPE-biotin in the absence of neutravidin is broad and the absorption shows a red-shifted band max at 470 nm, indicating that the polymer is aggregated in the aqueous PBS solution.[38,39] Interestingly, with increasing concentration of neutravidin, the absorption maximum of PPE-biotin blue-shifts from 470 to 430 nm and the fluorescence maximum also shifts from 570 to 480 nm (FIG. 3*b*). Taken together, these effects suggesting that neutravidin leads to de-aggregation of the PPE-biotin. It is likely that the binding of the biotin units to the neutravidin leads to a "protein coating" on the polymer which reduces the interchain interactions that are characteristic of the aggregated polymer. In contrast, the absorption and fluorescence spectra of PPE did not change much with the increasing concentration of neutravidin (FIG. 3*c* and FIG. 3*d*), consistent with only a weak interaction between PPE and the biotin-binding protein.

Figures 4A, 4B, 4C, 4D:
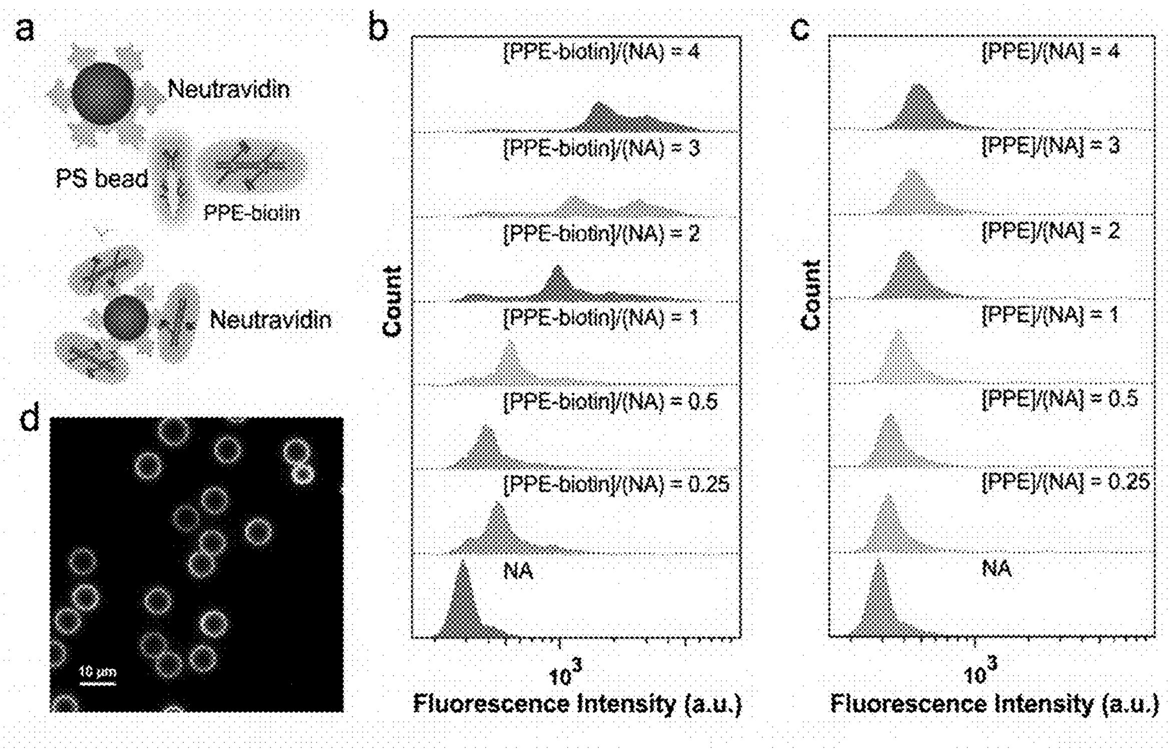
FIG. 4*a*-4*d*. (a) Illustration of the binding of PPE-biotin with neutravidin coated beads. (b) and (c) The fluorescence intensity of neutravidin coated beads with the incubation of different concentration of PPE-biotin and PPE. The concentration of the neutravidin was 33 nM. The concentration ratios of [PPE-biotin]/[neutravidin] were 4, 3, 2, 1, 0.5 and 0.25, respectively. The laser wavelength was 405 nm, and the fluorescence detection channel was 450±50 nm. Thirty thousand events were recorded for each sample. (d) Fluorescence image of neutravidin coated beats with the treatment of PPE-biotin. The concentration ratio of [PPE-biotin]/[neutravidin] was 4. The laser wavelength was 405 nm and the detection was selected by a 425 nm long pass filter.

Flow cytometry is frequently used to analyze the physical and chemical characteristics of cells or particles. Although a variety of fluorescent labels have been developed for flow cytometry, and some are commercially available, more novel functional agents are still needed. Conjugated polymers with large molar absorption coefficients, high fluorescence quantum yield, and excellent light stability are promising materials for application as high brightness fluorescence labels for flow cytometry. However, there are few reports of their use as flow cytometry labels or probes. 40-41 Herein we report a proof of concept study that relies on the affinity of PPE-biotin to bind to neutravidin coated polystyrene beads (FIG. 4*a*). In this study, commercial neutravidin coated polystyrene microspheres that are 6-8 μm in diameter were used. Each surface bound neutravidin has on average two accessible biotin binding sites, while the other two sites are used to bind the protein to the polystyrene bead surface. The microspheres were pre-mixed with aliquots of PPE-biotin (m=53%), and then the mixtures were analyzed by flow cytometry. The excitation was at 405 nm and fluorescent detection was at 450 nm. As seen in FIG. 4*b*, as the PPE-biotin concentration increased, the detected fluorescence intensity of the beads increased by up to an order of magnitude (FIG. 4*b*). By contrast, addition of PPE (without biotin groups) to the beads did not lead to a significant change in the fluorescence intensity (FIG. 4*c*). The difference in behavior of the PPE-biotin is clearly due to the binding of the polymer to the beads via the biotin-neutravidin interaction.

Careful inspection of the data in FIG. 4*b* shows that the fluorescence from the PPEbiotin/neutravidin beads exhibits several peaks, suggesting a heterogeneous distribution of beads is present in the samples. The inventors hypothesize that this behavior is due to bead "aggregates" formed by crosslinking due to the fact that the PPE-biotin chains have multiple biotin units available for binding to more than a single bead. Inspection of the forward-scattering plots from the flow cytometry data reveals the presence of particles that are larger, likely due to particle dimers and trimers. Confocal microscope images were obtained on a PPE-biotin/neutravidin bead sample (PPE-Biotin:neutravidin 4:1) and it is possible to observe the bright fluorescence characteristic of the polymer on the surface of the beads (FIG. 4*d*). Interestingly, it is possible to observe 3 distinct bead dimers in the image, supporting the assignment of the multiple peaks in the flow cytometry data to particle dimers or aggregates. Taken together, these results show the promise of bio-functionalized PPE to be used as an effective fluorescent label in flow cytometry studies.

Materials. Organic solvents were purchased from Sigma-Aldrich and dried by elution through an MBruan MB-SPS-800 solvent purification system. Compounds 1 and 2 were synthesized according to the literature.[25,26] Neutravidin coated beads were purchased from Spherotech, Inc. Other chemicals were purchased from Sigma-Aldrich Chemical Company and Fisher Scientific and used as received. Deionized water (18.2 MQcm) was obtained from a MilliQ system (Millipore, Bedford, MA). 6-8 kDa molecular weight cutoff dialysis membranes were purchased from Fisher Scientific.

Measurements. $^1H$ NMR spectra were recorded on a Bruker Advance 500 MHz spectrometer. UV-visible absorption spectra were measured on a Shimadzu UV-2600 spectrophotometer. Corrected steady-state emission spectra were measured on an Edinburgh FLS 1000 photoluminescence spectrometer. The absolute fluorescence quantum yield was recorded on an integrating sphere. Gel permeation chromatography analysis was recorded on an EcoSEC GPC system using polystyrene standards with THF as eluent. Flow cytometry data were collected by using BD Biosciences LSR-11 instrument. Confocal fluorescence microscope images were taken on MicroTime 200 time-resolved fluorescence microscope (PicoQuant). The excitation was provided by a 405 nm diode laser and detection was selected by a 425 nm long pass filter.

Flow Cytometry Analysis. In a series of 5 mL polystyrene tubes, a portion of PBS buffered solution (268 μL, pH=7.4) followed by the addition of a PBS solution of neutravidin coated polystyrene beads (32 μL, $2.86\times10^7$ particles/mL, $6.48\times10^6$ neutravidin/particle, the concentration of neutravidin is 0.31 μMin the stock solution). The appropriate volume of 10 μM stock solution of PPE-biotin was added into the tube accordingly. The same procedure was repeated for a 10 μM stock solution of PPE. The solutions were allowed to sit for 2 hours before being processed by the flow cytometer. On a BD Biosciences LSR-11 flow cytometer, the 405 nm laser was used as excitation light and Pacific Blue detection channel (450±50 nm) was selected to collect the fluorescence of polymer. Each tube was inserted and the solution was drawn at a medium flow rate until 30,000 events were recorded in each sample. Gating and other statistics were obtained through FlowJo v10.

Example 2

One- and Two-Photon Activated Chemotherapy of Pt(IV)-Functionalized Poly(Phenylene Ethynylene) Operating Via Intramolecular Electron Transfer One and two-photon activated water-soluble poly(phenylene ethynylene) polymer, PPE-Pt(IV), functionalized with oxidized oxaliplatin Pt(IV) in the side chains can be used for light-controlled chemotherapy. The photoactivation strategy is based on intramolecular photoinduced electron transfer from electron-rich PPE backbones to electron acceptor Pt(IV) complexes to generate oxaliplatin, a clinical anticancer drug. This photoactivation process performed effectively, producing oxaliplatin with chemical yields of above 70% and 90% in the absence and presence of ascorbate, respectively. Notably, PPE-Pt(IV) was inert to cancer cells in the dark but under short-period irradiation, Pt(IV) complex was rapidly reduced to oxaliplatin, thereby turning on the anticancer activity for ovarian cancer cells. The controllable activation property of PPE-Pt(IV) offers the prospect of photocages with new mechanisms of action and suggests a strategy for the design of two-photon activatable prodrugs to reduce the side effects of traditional platinum chemotherapy.

A. Results

Polymer preparation. The synthesis of PPE-Pt(IV) is outlined in Scheme 4. Oxaliplatin Pt(II) was oxidized by hydrogen peroxide to afford oxaliplatin$(OH)_2$(ox) Pt(IV) according to the literature.[73,74] PPE-Pt(IV) was obtained by the esterification reaction of water-soluble PPE with oxaliplatin$(OH)_2$(ox) Pt(IV) using 1-ethyl-3-(3-dimethylaminopropyl) carbodiimide (EDCI) and N-hydroxysuccinimide (NHS) as the coupling reagents in an aqueous solution. The extent of reaction of the available carboxyl units from PPE was 25% as assessed by analysis of the $^1H$ NMR (There is one oxaliplatin$(OH)_2$(ox) loaded every two repeat units). With the sulfonate and carboxylate groups on the sidechains, PPE-Pt(IV) was soluble in water at room temperature. The UV-visible absorption spectrum of PPE-Pt(IV) in water features a maximum at 443 nm with a molar absorption coefficient of $3.4\times10^4$ $L\cdot mol^{-1}\cdot cm^{-1}$ and a shoulder peak at 461 nm. Compared with the single absorption peak of PPE at 441 nm, the shoulder absorption peak of PPE-Pt(IV) indicates the aggregations of the polymer due to the decreased number of carboxylate groups and limited solubility of oxaliplatin$(OH)_2$(ox) on the sidechains. The aggregation is also recognized by fluorescence spectra. The spectral shape of PPE shows clear vibronic structure with narrow bandwidth for the 0-0 transition at 460 nm. In contrast, emission from PPE-Pt(IV) shows a broad and bathochromically shifted band at 490 nm.

Scheme 4. Synthesis of PPE-Pt(IV).

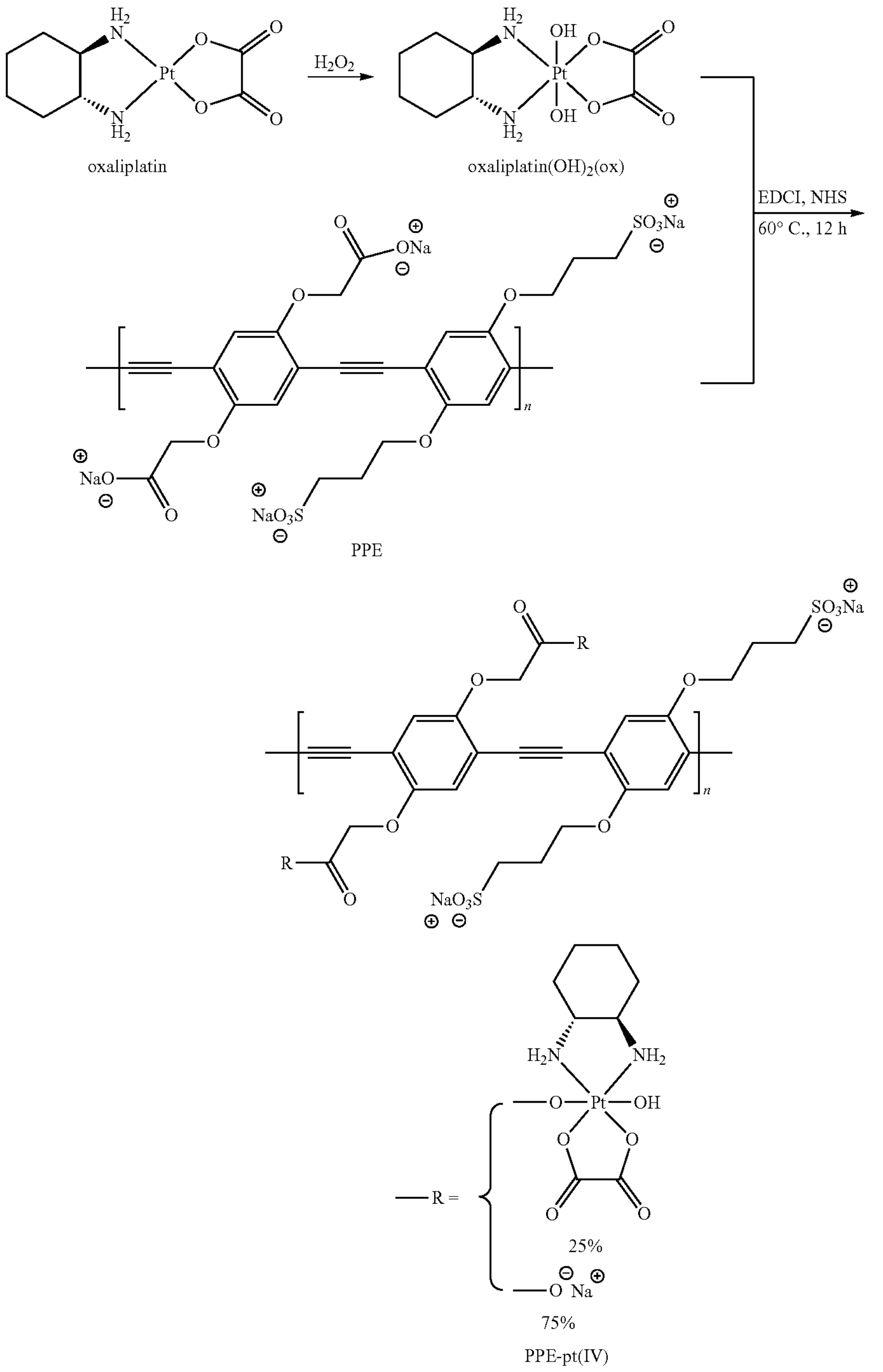

oxaliplatin oxaliplatin$(OH)_2$(ox)

PPE

PPE-pt(IV)

Figures 7A, 7B, 7C, 7D, 7E, 7F:
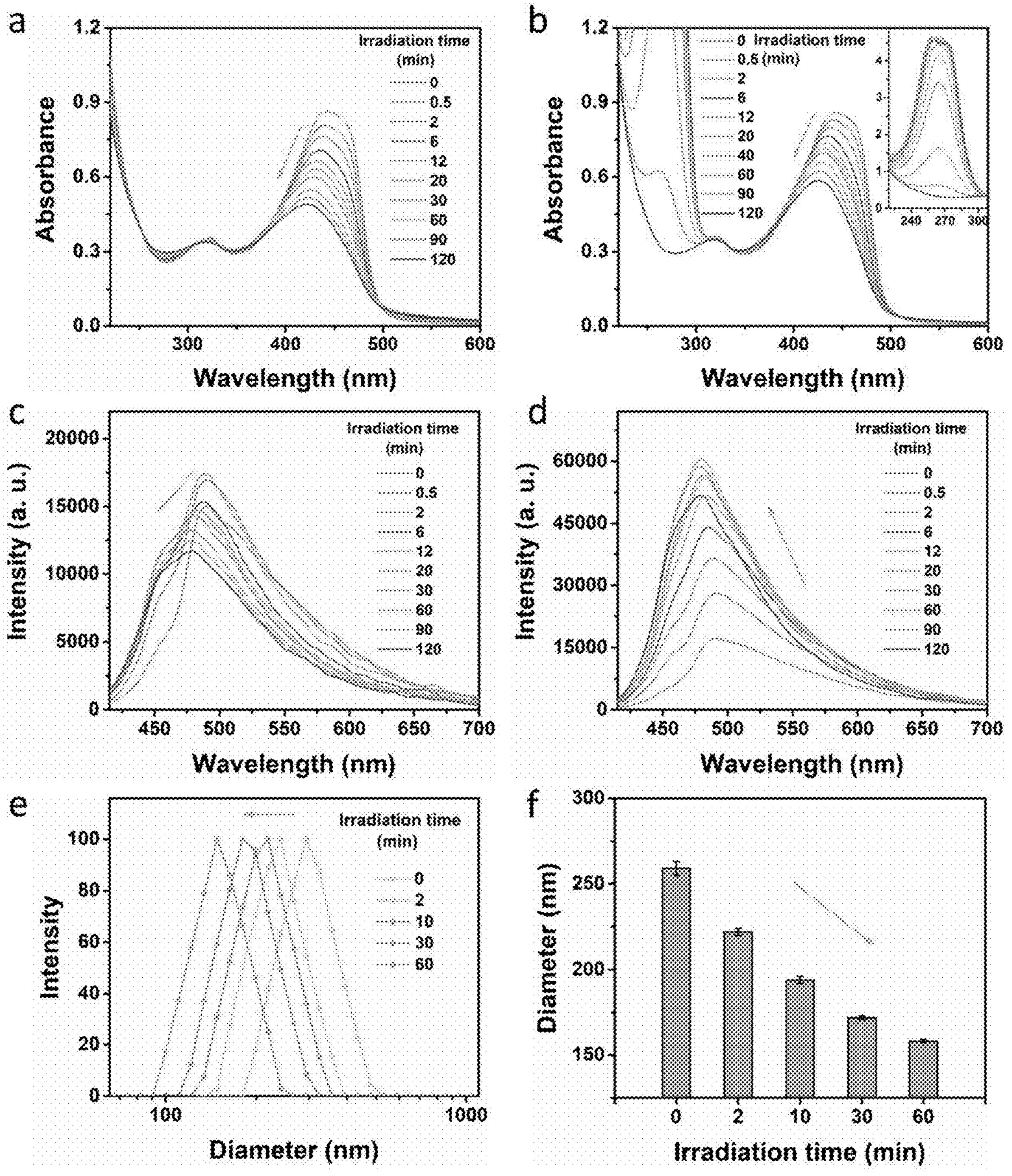
FIG. 7*a*-7*f*. The UV-visible absorption and emission spectra of PPE-Pt(IV) (25 μM) without (a, c) and with (b, d) NaAs (0.5 mM) in water for different irradiation time. The excitation wavelength is 405 nm. The irradiation was carried out using a 400 nm LED light with a power density of 5 mW/$cm^2$. (e) and (f) Hydrodynamic diameters of PPE-Pt (IV) (25 μM) with different irradiation time.

Uncaging studies. The photoreduction properties of PPE-Pt(IV) was evaluated in a series of one-photon irradiation experiments. The UV-visible absorption and emission spectra and dynamic light scattering (DLS) measurement were performed. Given that sodium ascorbate (NaAs) is a commonly used sacrificial donor in electron transfer system and is abundant in cells, it is hypothesized that NaAs might accelerate the photoreduction process. As shown in FIG. 7*a*, with increasing time of irradiation, the shoulder absorption peak at 461 nm disappeared and the absorption maximum at 443 nm blue-shifted slightly, indicating that PPE-Pt(IV) was deaggregated with the release of oxaliplatin with time. The changes in absorption spectra of PPE-Pt(IV) in the presence of NaAs with irradiation time showed a similar trend as PPE-Pt(IV) (FIG. 7*b*). Almost all of the NaAs was consumed within 2 h of irradiation. The fluorescence intensity of PPE-Pt(IV) did not exhibit significant changes. However, the emission at 450 nm becomes more dominant after irradiation (FIG. 7*c*). In contrast, the fluorescence of PPE-Pt(IV) with NaAs undergoes a significant increase along with irradiation time, accompanied by a blue shift in the emission peak (FIG. 7*d*). It is contemplated that NaAs improved the extent of the photoreaction by two ways: (1) NaAs was oxidized by the reaction intermediate PPE radical cation, which accelerated the electron transfer process; (2) NaAs could protect PPE-Pt(IV) from photobleaching by consuming reactive oxygen species. In the absence of NaAs, the nearly unchanged fluorescence intensity and blue shifted spectra indicated an insufficient release of oxaliplatin from polymer sidechains. In contrast, the significantly increased fluorescence intensity in the presence of NaAs suggested a higher photoreaction efficacy. DLS measurement was employed to monitor the hydrodynamic diameter changes of PPE-Pt(IV) during irradiation. PPE-Pt(IV) displayed a diameter of 259 nm in water. As the irradiation time increased, the diameter decreased to 194 nm at 10 min and further decreased to 158 nm after 60 min (FIGS. 7*e* and 7*f*). Taken together these results demonstrated that PPE-Pt(IV) is capable of a light-dependent release of oxaliplatin and that this photoreduction process is more efficient in the presence of NaAs.

Photoactivation properties of PPE-Pt(IV) were investigated quantitatively by high performance liquid chromatography (HPLC). The polymers were removed by ultrafiltration tubes with a molecule weight cutoff of 10 KD before the samples were injected to the HPLC column. The stability of PPE-Pt(IV) in the dark was studied firstly. In the presence of 1 mM NaAs (20 equivalent to the repeat unit of PPE-Pt(IV)), the amount of generated oxaliplatin in water was detected at 12, 24, and 48 h, respectively. The concentration of PPE-Pt (IV) repeat unit was 50 If all the oxaliplatin$(OH)_2$(ox) in the sidechains are reduced, the theoretical amount of oxaliplatin produced should be 25 μM according to the 25% substitution of oxaliplatin$(OH)_2$(ox) over the carboxylate groups (There are two carboxylate groups on each repeat unit of PPE. Thus, the loading of oxaliplatin$(OH)_2$(ox) on each repeat unit of PPE-Pt(IV) is 50%.). The yield of oxaliplatin was calculated as the concentration of generated oxaliplatin over 25 μM. As shown in FIG. 8*a*, only about 8% of oxaliplatin was generated after 24 h. The representative HPLC chromatograms were displayed in FIG. 8*b*. Very weak peaks of oxaliplatin were detected at the retention time of 5.99 min, suggesting the good dark stability of PPE-Pt(IV) in the presence of extra reducing agent.

One-photon uncaging of PPE-Pt(IV) (50 μM) was monitored in water solutions under a 400 nm LED light. Oxaliplatin was produced fast within 10 min (FIG. 8*a*). The chemical yield reached to about 60% when PPE-Pt(IV) was exposed to light for 0.5 h. The formation of oxaliplatin was also confirmed by high resolution ESI-Mass by analyzing the fraction collected at the retention time of 5.99 min. The addition of NaAs improved the photoreduction process, resulting in a chemical yield of oxaliplatin above 90% after irradiation for 0.5 h (FIG. 8*a*). Although a small amount of oxidized oxaliplatin was detected by HPLC at the retention time of 4.13 min (FIG. 8*b*), oxaliplatin was the major product from the photolysis reaction. Two-photon uncaging of PPE-Pt(IV) was also studied since a structurally-similar PPE-type polyelectrolyte has been demonstrated to have superior two-photon absorption abilities, especially in its aggregation state. 26 Nearly a chemical yield of 50% was obtained in the presence of NaAs after PPE-Pt(IV) was irradiated for 1 h under a 725 nm laser (FIG. 8*a*, 8*b*), suggesting the potential in vivo applications of this approach.

Photoreduction mechanism of PPE-Pt(IV). The mechanism of the photoreduction was further studied. The fluorescence quantum yield of PPE-Pt(IV) was 0.013, which is much more lower than that of PPE (Table 2). This low fluorescence quantum yield of PPE-Pt(IV) indicated efficient quenching of the singlet excited state, presumably due to the photoinduced electron transfer from the singlet excited state of PPE to Pt(IV) center on the sidechains. The fluorescence lifetime of PPE-Pt(IV) also decreased significantly comparing with that of PPE (Table 2). The electron transfer efficiency can be estimated from eq 1, $$\eta=1-[\Phi_f(\text{PPE-Pt(IV)})/\Phi_f(\text{PPE})] \quad (1)$$

As expected, PPE-Pt(IV) exhibited a high yield of charge transfer (η=93%), implying a fast and efficient photon induced electron transfer process.

TABLE 2

Fluorescence Lifetimes and Quantum Yields of PPEs in Water

| | τ/ns (normalized amplitude)[a] | $\Phi_f^b$ |
|---|---|---|
| PPE | 0.16 (0.89), 0.38 (0.11) | 0.19 |
| PPE-Pt(IV) | 0.017 (0.96), 0.22 (0.036), 0.92 (0.009) | 0.013 |

[a]Multiexponential decays. Decay lifetimes reported in nanoseconds, and the normalized amplitudes of each decay component are in parenthesis.
[b]Quantum yields measured by the absolute method using an integrating sphere with water as the reference.

The fundamental requirement for efficient photon induced electron transfer is that the Gibbs free energy ($\Delta G_{PET}$) for the process should be negative. The driving force for charge separation from the singlet excited state of PPE-Pt(IV) can be approximated by using eq 2

$$\Delta G_{PET}=e(E_{OX}-E_{RED})-\Delta E_{0,0}-e^2/(4\pi\varepsilon_0\varepsilon R_{DA}) \quad (2)$$

where $E_{OX}$ is the oxidation potential of the donor (PPE, 0.70 V vs. SCE[34]), ERE D is the reduction potential of the acceptor (Pt(IV), −0.85 V vs. SCE[76]), and $\Delta E_{0,0}$ is the singlet excited state energy which is estimated on the basis of $\Delta E_{0,0}=((E_{abs(max)}+E_{em(max)})/2$ (2.75 eV). The last term is the Coulomb stabilization energy of the charges, where $\varepsilon_0$ is the vacuum permittivity, ε is the dielectric constant of the solvent, and $R_{DA}$ is the distance of charge separation. Since the ε is large for water (ε=80.4), the Coulomb stabilization energy can be ignored in this system. Thus, the free Gibbs energy for photo induced electron transfer calculated according to eq 2 is −1.20 eV, suggesting that the process is strongly favorable.

To obtain more insight into the photo induced electron transfer process of PPE-Pt(IV), picosecond transient absorption (TA) measurements were performed. PPE was employed as control for better understanding the nature of PPE-Pt(IV). The TA spectrum of PPE is similar to those of reported other water-soluble PPEs. 77 As shown in FIG. 9*a*, the negative signal observed between 430-520 nm is attributed to the simulated emission of PPE, and the broad positive signal between 520-700 nm is assigned to the excited-state absorption (ESA). In contrast, the TA spectrum of PPE-Pt(IV) is quite different from that of PPE. The simulated emission is weaker due to the fluorescence quenching in PPE-Pt(IV), which results in a stronger absorption in the region between 480-540 nm (FIG. 9*b*). For more information, the kinetics of PPE and PPE-Pt(IV) at 661 nm are displayed and fitted in FIG. 9*c* and Table 3, respectively. The ESA kinetic of PPE exhibits three-exponential decay components with time constants of 1.7, 29.9 and 245 ps with relative amplitudes of about 0.43, 0.29 and 0.28, respectively. The faster decay can be attributed to the initial structural relaxations and nonradiative processes. The longer lifetime of 245 ps is most likely from the fluorescence emission, which is in good agreement with the fluorescence decay kinetics (Table 2). Overall, the kinetic of PPE-Pt(IV) exhibits evidently faster decay than that of PPE. It is contemplated that the TA spectrum of PPE-Pt(IV) is dominated by the absorption of the oxidized polymer ($PPE^{-+}$). This is supported by a research, in which a similar absorption-difference spectrum was also observed from a structurally-similar PPE-based polymer cation radical generated by pulse radiolysis.[78] And it is not unusual for conjugated polymers to have similar TA spectra in exciton and polaron state.[79] Based on these result, the inventors propose a photoactivation mechanism of PPE-Pt(IV). Upon irradiation, PPE-Pt(IV) is excited to singlet excited state, PPE*-Pt(IV). Then, one electron is transferred from PPE* to Pt(IV) center to yield a Pt(III) complex along with the disassociation of the axial ligand. The formed Pt(III) complex is unstable, which will quickly be converted to oxaliplatin Pt(II).

TABLE 3

| Picosecond Transient Absorption Kinetics | |
|---|---|
| | τ/ps (normalized amplitude)[a] |
| PPE | 1.7 ± 0.1 (0.43), 29.9 ± 3.6 (0.29), 245 ± 20 (0.28) |
| PPE-Pt(IV) | 0.63 ± 0.08 (0.54) 9.6 ± 1.1 (0.31), 350 ± 44 (0.15) |

[a]Multiexponential decays. Decay lifetimes reported in picoseconds, and the normalized amplitudes of each decay component are in parenthesis.

Biological activity of PPE-Pt(IV) against cancer cells. It is hypothesized that the light-dependent uncaging and photoreduction of PPE-Pt(IV) to promote oxaliplatin release would allow the conjugate polymer to be used as a light-activated prodrug to allow for regulated cytotoxicity of cancer cells in culture. The effects of 2.5-10 μM PPE-Pt(IV) were evaluated in SK-OV-3 human ovarian cancer cells as compared to PPE or oxaliplatin alone under both light activated and dark conditions. The effective concentration of oxaliplatin indicated for these comparative studies is twice the actual oxaliplatin concentration used due to an effective 50% loading of the Pt(IV) complex on each polymer repeat unit where 10 μM of PPE-Pt(IV) could optimally liberate 5 μM of oxaliplatin upon light activation.

Figures 10A, 10B, 10C, 10D:
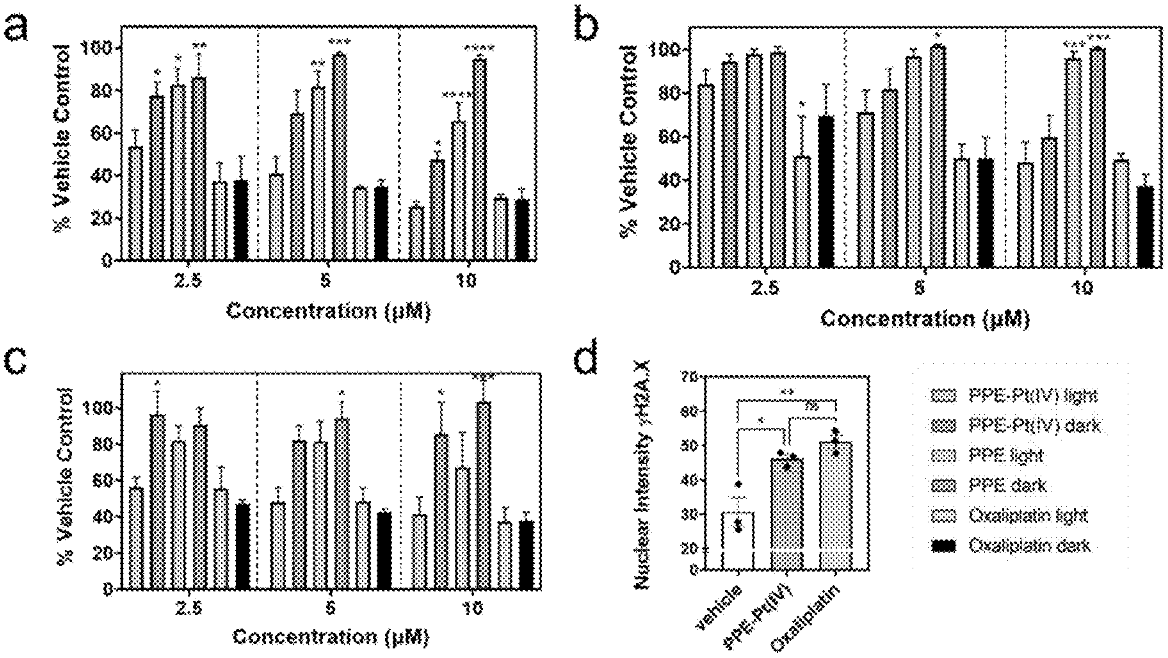

SK-OV-3 cells were first treated with PPE-Pt(IV) or controls for 24 h prior to light activation and then cell viability was evaluated after an additional 48 h. At each concentration, PPE-Pt(IV) showed a light-dependent decrease in cell viability that was comparable to the effective concentration of oxaliplatin alone (FIG. 10*a*). The effects of light-activated PPE-Pt(IV) on cell viability were significantly greater than PPE alone, either in light or dark conditions (FIG. 10*a*), although there appeared to also be some effect of light-activated PPE at 10 μM, probably resulting from the generation of reactive oxygen species.[80] To determine whether the light-activated bioactivity of PPE-Pt(IV) was due primarily to polymer that was taken up into cells prior to light activation or as a result of activation of polymer in the extracellular media, the same experiment was performed with the addition of a wash step immediately before light activation to remove any unincorporated polymer from the media. It was found that the light-dependent activity of the PPE-Pt(IV) polymer was effectively reduced at every concentration evaluated when the media was replaced (FIG. 10*b*), suggesting that the majority of light-dependent bioactivity was due to the activation of polymer in the extracellular medium.

To further test the hypothesis that activation of PPE-Pt (IV) in the extracellular media was sufficient to observe the light-dependent cytotoxicity observed in FIG. 10*a*, this experiment was repeated with a decreased the preincubation period from 24 h to 1 h prior to light activation. Indeed, a light-dependent effect of PPE-Pt(IV) on the cell viability was observed that was similar to the effect of an equivalent concentration of oxaliplatin alone (FIG. 10*c*). This same phenotype was observed in another human ovarian cancer cell line, OV-90. Together, these data demonstrate that PPE-Pt(IV) can effectively serve as a light-activated prodrug that could improve the therapeutic window of oxaliplatin by allowing for temporal and special activation in the local tumor microenvironment.

To ensure that the mechanism by which PPE-Pt(IV) was inhibiting cell viability upon light activation was consistent with the cellular uptake and DNA binding of oxaliplatin, immunofluorescence of phosphorylation of histone H2A.X at serine 139 (γH2A.X) was used as a marker of DNA damage. It was found that, within 18 h of light activation, PPE-Pt(IV) increased the nuclear intensity of this DNA damage marker to the same extent as an equivalent concentration of oxaliplatin that was released (FIG. 10*d*). These data demonstrate that the decrease in cell viability observed upon light activation of PPE-Pt(IV) is consistent with release of the DNA damaging chemotherapeutic, oxaliplatin, into the medium. Taken together, these data demonstrate that the caging of oxaliplatin by PPE provides an innovative and a strategic method of regulated delivery of this chemotherapeutic that could be utilized to decrease toxicity and enhance specificity.

The inventors have designed and synthesized a novel water-soluble conjugated polymer functionalized with Pt(IV) complex as a prodrug for photoactivable chemotherapy. Upon irradiation, PPE-Pt(IV) undergoes electron transfer from singlet excited state of PPE to Pt(IV) complex to generate oxaliplatin with a chemical yield above 70%. The photoreaction yield can be raised to over 90% in the presence of NaAs, which protected PPE-Pt(IV) from photobleaching and accelerated the electron transfer process. More importantly, PPE-Pt(IV) can also be activated by two photon absorption at 725 nm with a moderate yield, suggesting potential in vivo applications of this approach. Furthermore, A light-dependent effect of PPE-Pt(IV) on the cell viability has observed over two human ovarian cancer cell lines. This work offers an approach to the rational design of photocages and also opens up a new direction for the development of platinum drug with controllable activation properties to reduce adverse effects.

The examples provided herein as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

REFERENCES (1) Kini et al., *Adv. Mater.* 2020, 32, 1906175.
(2) Bronstein et al., *Nat. Rev. Chem.* 2020, 4, 66-77.
(3) Gao et al., *Polymers* 2017, 9, 42.
(4) Li et al., *Acc. Chem. Res.* 2016, 49, 78-85.
(5) Fu et al., *Angew. Chem., Int. Ed* 2019, 58, 4442-4453.
(6) Zhang et al., *Chem. Soc. Rev.* 2020, 49, 1331-1343.
(7) Hwang et al., *ACS Appl. Mater. Interfaces* 2020, 12, 8485-8494.
(8) Chen et al., *Chem. Rev.* 2020, 120, 2879-2949.
(9) Chen et al., *ACS Appl. Mater. Interfaces* 2020, 12, 6144-6150.
(10) Wang et al., *Coard Chem. Rev.* 2018, 354, 135-154.
(11) Traina et al., *J Am. Chem. Soc.* 2011, 133, 12600-12607.
(12) Nie et al., *Small* 2015, 11, 2555-2563.
(13) Wang et al., *ACS Appl. Mater. Interfaces* 2015, 7, 24110-24118.
(14) Wu et al., *Chem. Commun.* 2014, 50, 2040-2042.
(15) Kim et al., *Bioconjugate Chem.* 2007, 18, 815-820.
(16) Senthilkumar et al., *Angew. Chem., Int. Ed* 2018, 57, 13114-13119.
(17) Lee et al., *Adv. Enna. Mater.* 2007, 17, 2580-2587.
(18) Lee et al., *Adv. Mater.* 2012, 24, 2479-2484.
(19) Feng et al., *J Mater. Chem.* 2010, 20, 1312-1316.
(20) Zhou et al., *Acc. Chem. Res.* 2019, 52, 3211-3222.
(21) Anantha-Iyengar et al., *Frog. Polym. Sci.* 2019, 88, 1-129.
(22) Haldon et al., *Org. Biomol. Chem.* 2015, 13, 9528-9550.
(23) Lang et al., *ACS Chem. Biol.* 2014, 9, 16-20.
(24) Hoyle et al., *Angew. Chem., Int. Ed* 2010, 49, 1540-1573.
(25) Zhang et al., *Macromolecules* 2006, 39, 7839-7843.
(26) Jagadesan and Schanze, *Macromolecules* 2019, 52, 3845-3851.
(27) Dundas et al., *Appl. Microbial. Biotechnol.* 2013, 97, 9343-9353.
(28) Ward, *Acc. Chem. Res.* 2011, 44, 47-57.
(29) Ren et al., *Chem. Commun.* 2015, 51, 10403-10418.
(30) Kamperman et al., *Nat. Commun.* 2019, 10, 4347.
(31) Wang et al., *Angew. Chem., Int. Ed* 2019, 58, 14026-14043.
(32) Gu et al., *ACS Appl. Mater. Interfaces* 2019, 11, 47720-47729.
(33) Phillips et al., *Macromolecules* 2008, 41, 7316-7320.
(34) Stratton et al., *Chem.-Eur. J* 2017, 23, 14064-14072.
(35) Chen et al., *Chem. Rev.* 2012, 112, 1910-1956.
(36) Xia et al., *Anal. Chem.* 2017, 89, 1238-1243.
(37) There is also a red-shift and slight increase in the PPE absorption with decreasing pH which is attributed to aggregation of the polymer as the residual —$CO2^-$ units are protonated and the overall charge on the polymer decreases.
(38) Lee et al., *Macromolecules* 2011, 44, 4742-4751.
(39) Jiang et al., *Langmuir* 2006, 22, 5541-5543.
(40) Feng et al., *Adv. Mater.* 2012, 24, 637-641.
(41) Wang et al., *Chem. Commun.* 2016, 52, 4022-4024.
(42) Stanley et al., *Science,* 2012, 336, 604-608.
(43) Pan et al., *Proc. Natl. Acad Sci. U S. A.,* 2018, 115, 992-997.
(44) Kong et al., *Adv. Sci.,* 2021, 8, 2100962.
(45) Huang et al., *Nat. Nanotechnol.,* 2010, 5, 602-606.
(46) Krawczyk et al., *Science,* 2020, 368, 993-1001.
(47) Bhokisham et al., *Nat. Commun.,* 2020, 11, 2427.
(48) Xiong et al., *Adv. Funct. Mater.,* 2020, 30, 1903896.
(49) Zhao et al., *Small,* 2019, 15, 1903060.
(50) Cho et al., *Nat. Mater.,* 2012, 11, 1038-1043.
(51) Chen et al., *Adv. Sci.,* 2020, 7, 1903783.
(52) Yun and Kwok, *Nat. Biomed. Eng.,* 2017, 1, 0008.
(53) Ankenbruck et al., *Angew. Chem. Int. Ed.,* 2018, 57, 2768-2798.
(54) Zhang et al., *Adv. Mater.,* 2020, 32, 2002661.
(55) Bai et al., *Proc. Natl. Acad. Sci. U S. A.,* 2003, 100, 409-413.
(56) Tang et al., *Angew. Chem. Int. Ed.,* 2020, 59, 18386-18389.
(57) Shen et al., *Acta Biomater.,* 2020, 115, 75-91.
(58) Karges et al., *Dalton Trans.,* 2021, 50, 2757-2765.
(59) Jana et al., *ACS Nano,* 2014, 8, 5939-5952.
(60) Goswami et al., *J. Am. Chem. Soc.,* 2015, 137, 3783-3786.
(61) Kand et al., *J. Am. Chem. Soc.,* 2020, 142, 4970-4974.
(62) Zhu et al., *Chem. Rev.,* 2012, 112, 4687-4735.
(63) Zhou et al., *Acc. Chem. Res.,* 2019, 52, 3211-3222.
(64) Lu et al., *Polym. Chem.,* 2018, 9, 3118-3126.
(65) Wang et al., *Chem. Mater.,* 2017, 29, 3295-3303.
(66) Parthasarathy et al., *ACS Appl. Mater. Interfaces,* 2010, 2, 2744-2748.
(67) Valandro et al., *J. Phys. Chem. Lett.,* 2020, 11, 8292-8296.
(68) Conteduca et al., *BMC Cancer,* 2018, 18, 1267.
(69) Fracasso et al., *Clin. Oncol.,* 2003, 21, 2856-2859.
(70) Wang and Lippard, *Nat. Rev. Drug Discovery,* 2005, 4, 307-320.
(71) Martinez-Balibrea et al., *Mol. Cancer Ther.,* 2015, 14, 1767-1776.
(72) Hall et al., *J. Med. Chem.,* 2007, 50, 3403-3411.
(73) Feng et al., *Adv. Funct. Mater.,* 2016, 26, 7431-7442.
(74) Bantle et al., *Eur. J. Inorg. Chem.,* 2014, 2014, 484-492.
(75) Yang, University of Florida, 2019.
(76) Wang et al., *Chem,* 2019, 5, 3151-3165.
(77) Jagadesan et al., *Mater. Chem. Front.,* 2020, 4, 3649-3659.
(78) Funston et al., *J. Phys. Chem. B,* 2004, 108, 1544-1555.
(79) Patil et al., *Chem. Rev.,* 1988, 88, 183-200.
(80) Jagadesan et al., *Chem. Mater.,* 2020, 32, 6186-6196.

The invention claimed is:

1. A water-soluble conjugated polymer comprising a base polymer coupled to one or more ligands, the conjugated polymer having a structure of Formula III Formula III

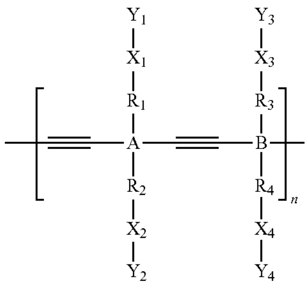

wherein n can be any whole number between 2 and 500;
A and B are aryl or heteroaryl;
R1, R2, R3, and R4 are independently selected from a Cl to C12 alkoxy, Cl to C12 alkyl, or $(CH_2CH_2O)_m$, where m is 2, 3, 4, 5, 6, 7, 8, 9, 10;
X1 and X2 are carboxylic;
X3 and X4 are sulfonic; and
Y1, Y2, Y3, and Y4 can be H, or a detectable ligand, or therapeutic ligand, or a diagnostic ligand.

2. The polymer of claim 1, wherein A and B are phenyl.

3. The polymer of claim 1, wherein R1 and R2 are Cl alkoxy and R3 and R4 are C3 alkoxy.

4. The polymer of claim 1, wherein 1, 2, 3, 4, 5, or more ligands can be conjugated to the polymer.

5. The polymer of claim 4, wherein 2 or more different ligands are conjugated to the polymer.

6. The polymer of claim 1, wherein the ligand is coupled to the polymer by a linker.

7. The polymer of claim 6, wherein the linker is labile linker.

8. The polymer of claim 7, wherein the labile linker is a photo-labile linker.

9. The polymer of claim 7, wherein the polymer is a prodrug.

10. A therapeutic method comprising administering a therapeutic conjugate of claim 1 to a subject in need thereof.

11. An analytical method comprising contacting a sample with a conjugate of claim 1 and detecting a signal derived from the conjugate.

12. A diagnostic method comprising administering a conjugate of claim 1 to a subject or sample and detecting a signal derived from the conjugate.

* * * * *